(12) United States Patent
Gautier et al.

(10) Patent No.: US 11,162,951 B2
(45) Date of Patent: Nov. 2, 2021

(54) MEMBRANE-IMPERMEANT FLUOROGENIC CHROMOPHORES

(71) Applicants: PARIS SCIENCES ET LETTRES, Paris (FR); CENTRE NATIONAL DE LA RECHERCHE SCIENTIFIQUE, Paris (FR); INSTITUT CURIE, Paris (FR); SORBONNE UNIVERSITE, Paris (FR)

(72) Inventors: Arnaud Gautier, Paris (FR); Ludovic Jullien, Arcueil (FR); Chenge Li, Tai yuan (CN); Franck Perez, Paris (FR)

(73) Assignees: PARIS SCIENCES ET LETTRES, Paris (FR); CENTRE NATIONAL DE LA RECHERCHE SCIENTIFIQUE, Paris (FR); INSTITUT CURIE, Paris (FR); SORBONNE UNIVERSITE, Paris (FR)

( * ) Notice: Subject to any disclaimer, the term of this patent is extended or adjusted under 35 U.S.C. 154(b) by 129 days.

(21) Appl. No.: 16/612,018

(22) PCT Filed: May 18, 2018

(86) PCT No.: PCT/EP2018/063146
§ 371 (c)(1),
(2) Date: Nov. 8, 2019

(87) PCT Pub. No.: WO2018/211090
PCT Pub. Date: Nov. 22, 2018

(65) Prior Publication Data
US 2020/0124611 A1    Apr. 23, 2020

(30) Foreign Application Priority Data
May 19, 2017   (EP) .................................... 17305591

(51) Int. Cl.
*G01N 33/68*   (2006.01)
*G01N 21/76*   (2006.01)
*G01N 33/52*   (2006.01)
*C07D 277/36*  (2006.01)

(52) U.S. Cl.
CPC ....... *G01N 33/6803* (2013.01); *C07D 277/36* (2013.01); *G01N 21/76* (2013.01); *G01N 33/52* (2013.01)

(58) Field of Classification Search
CPC ..... G01N 33/582; G01N 21/77; C07D 401/06
See application file for complete search history.

(56) References Cited

FOREIGN PATENT DOCUMENTS

WO    WO-0018747 A1 *  4/2000  ........... C07D 493/04
WO    2016/001437 A2    1/2016

OTHER PUBLICATIONS

Plamont et al. Small fluorescence-activating and absorption-shifting tag for tunable protein imaging in vivo. PNAS 2016, vol. 13, No. 3, pp. 497-502. (Year: 2016).*
International Search Report dated Jul. 18, 2018 and Written Opinion in corresponding International application No. PCT/EP2018/063146; 9 pages.
Plamont et al., "Small fluorescence-activating and absorption-shifting tag for tunable protein imaging in vivo", Proceedings of the National Academy of Sciences the United States of America, Jan. 19, 2016, pp. 497-502, vol. 113, No. 3, https://doi.org/10.1073/pnas.1513094113.

* cited by examiner

*Primary Examiner* — Shafiqul Haq
(74) *Attorney, Agent, or Firm* — Maier & Maier, PLLC

(57) ABSTRACT

Fluorescent labeling of proteins. In particular, membrane-impermeant fluorogenic chromophores being capable of binding reversibly a functional derivative of a Photoactive Yellow Protein (PYP), or a functional fragment thereof, for fluorescently labeling biological molecules of interest, preferably proteins of interest. Especially, 4-hydroxybenzylidene-rhodanine (HBR) analogs of formula (II) as membrane-impermeant fluorogenic chromophores.

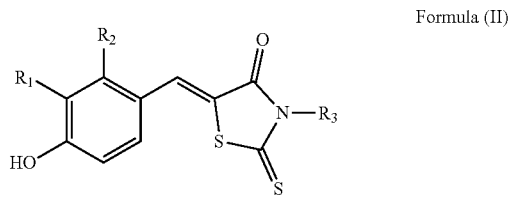

Formula (II)

9 Claims, 2 Drawing Sheets
Specification includes a Sequence Listing.

MEMBRANE-IMPERMEANT FLUOROGENIC CHROMOPHORES

FIELD

The present invention pertains to the field of fluorescent labeling of proteins. In particular, the present invention relates to membrane-impermeant fluorogenic chromophores being capable of binding reversibly a functional derivative of a Photoactive Yellow Protein (PYP), or a functional fragment thereof, for fluorescently labeling biological molecules of interest, preferably proteins of interest.

The present invention especially relates to 4-hydroxybenzylidene-rhodanine (HBR) analogs as membrane-impermeant fluorogenic chromophores.

BACKGROUND

The discovery of the green fluorescent protein (GFP) from *Aequorea victoria* has been essential in biomolecular imaging because genetic fusion with GFP allowed for the first time to study the dynamics of proteins in living systems. The discovery and development of new fluorescent proteins have facilitated multicolor imaging and biosensor design, and contributed to the emergence of super-resolution microscopy techniques. Although GFP-like fluorescent proteins enable to quantitatively localize proteins in living cells, they are not optimal for examining cellular events involving protein trafficking, redistribution and recycling. This is particularly true for processes involving membrane proteins. In particular, studying the function and organization of cell-surface proteins (e.g. transmembrane receptors, cell adhesion proteins) through GFP tagging is limited by fluorescence background originating from the concomitant labeling of cellular structures involved in biosynthesis, secretion and degradation of these proteins.

Methods to confine fluorescence to proteins anchored on the extracellular side of the membrane include the tagging of proteins with peptides that can be labeled with membrane-impermeant fluorophores. Common peptide tags to realize surface protein labeling are self-labeling tag, such as SNAP-tag/CLIP-tag or Halotag, and small peptides that can be modified with conjugating enzymes, such as biotin ligase and phosphopantetheine transferases. The labeling protocols associated to covalent protein labeling methods are however not optimal. Multiple reagents need to be added and/or several washing steps are necessary to eliminate fluorophore excess. Labeling kinetics is often slow, preventing the study of dynamic processes. Excess of fluorophore can reduce labeling time, but at the expense of selectivity and contrast. Last, the labeling is irreversible.

Fast fluorogenic labeling strategies aim to solve these issues by using non-covalent molecular recognition to activate the fluorescence of membrane-impermeant fluorogenic chromophores, so-called "fluorogens", that are otherwise non-fluorescent on their own. Non-covalent molecular recognition ensures faster labeling, as no chemical reaction is involved. Moreover, because unbound fluorogens are not fluorescent, no washing steps are needed, further increasing the temporal resolution of labeling. For example, membrane-impermeant malachite green derivatives recognized by fluorogen-activating proteins (FAPs) derived from single-chain antibodies allowed near-instantaneous labeling of surface exposed proteins. Prolonged exposure with some of these dyes was however reported to lead to non-specific labeling and partial cell penetration.

WO 2016/001437 patent application discloses new peptide tags comprising a photoactive yellow protein (PYP) functional derivative or a functional fragment thereof. In particular, WO 2016/001437 discloses the yellow fluorescence-activating and absorption-shifting tag (Y-FAST, hereafter "FAST"), which is a fluorogen-based reporter developed by the Applicant. FAST is a 14-kDa protein tag derived from the photoactive yellow protein (PYP) which can form complexes with various fluorogenic chromophores. FAST relies on two spectroscopic changes for fluorogen activation: increase of fluorescence quantum yield and absorption red shift. The additional absorption red-shift upon binding ensures higher imaging selectivity and contrast, as unbound or unspecifically bound fluorogen can be discriminated via the choice of the excitation wavelength. FAST is especially efficient in binding and activating the fluorescence of 4-hydroxybenzylidene rhodanine (HBR) and 4-hydroxy-3-methylbenzylidene rhodanine (HMBR):

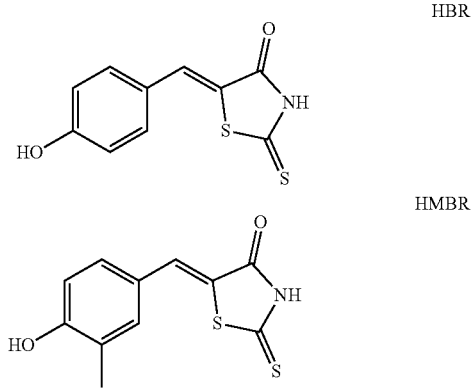

However, fluorogenic chromophores (such as HBR and HMBR) described in FAST-based labeling methods from prior art are membrane-permeant fluorogenic chromophores. Therefore, they cannot be used to selectively detect extracellular proteins, especially the extracellular domains of membrane proteins. Moreover, membrane-impermeant fluorogenic chromophores such as malachite green derivatives mentioned above are not compatible with FAST protein tag.

In order to provide investigators with the possibility of selectively detecting tagged cell-surface proteins, there is a need for novel fluorogens being incapable of crossing the cell membrane, while simultaneously being able to form sufficiently stable fluorescent complexes with protein tags, especially with FAST.

The Applicant thus conducted in-depth research about fluorogenic chromophores and surprisingly found that specific 4-hydroxybenzylidene-rhodanine (HBR) analogs could be used as potent membrane-impermeant fluorogenic chromophores.

SUMMARY

This invention relates to a complex formed by a compound of formula (II):

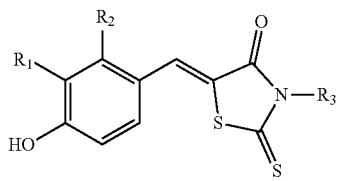

Formula (II)

wherein $R_1$ represents hydrogen, alkyl group having at least 2 carbon atoms or alkoxy group having at least 2 carbon atoms;

$R_2$ represents hydrogen, alkyl group or alkoxy group;

$R_3$ represents carboxyalkyl group wherein the alkyl part of the group comprises from 1 to 3 carbon atoms, preferably 1 or 2 carbon atoms, more preferably 1 carbon atom; and wherein exactly one group selected from $R_1$ and $R_2$ is hydrogen;

or a salt thereof;

with a photoactive yellow protein (PYP) functional derivative, or a functional fragment thereof.

According to an embodiment, $R_1$ represents an alkyl group comprising from 2 to 6 carbon atoms, preferably from 2 to 4 carbon atoms, more preferably 2 or 3 carbon atoms, or an alkoxy group comprising from 2 to 6 carbon atoms, preferably from 2 to 4 carbon atoms, more preferably 2 or 3 carbon atoms; $R_2$ represents hydrogen; and $R_3$ represents carboxymethyl group.

According to an embodiment, $R_1$ represents ethyl group; $R_2$ represents hydrogen; and $R_3$ represents carboxymethyl group.

According to an embodiment, $R_1$ represents hydrogen; $R_2$ represents an alkoxy group comprising from 1 to 6 carbon atoms, preferably from 1 to 4 carbon atoms, more preferably 1 or 2 carbon atoms; and $R_3$ represents carboxymethyl group.

According to an embodiment, the photoactive yellow protein (PYP) functional derivative, or a functional fragment thereof, binds the compound of formula (II) with a $K_D$ lower than about 15 µM; preferably lower than about 10 µM; when measured at a temperature of about 25° C.

This invention further relates to the use of a compound of formula (II) as previously described or a salt thereof, as membrane-impermeant fluorogenic chromophore.

According to an embodiment, the compound of formula (II) or a salt thereof is used in combination with at least one other fluorogenic chromophore; preferably in combination with a fluorogenic chromophore emitting in a different wavelength and/or a membrane-permeant fluorogenic chromophore; more preferably in combination with 4-hydroxybenzylidene rhodanine or 4-hydroxy-3-methylbenzylidene rhodanine.

This invention further relates to a method for detecting a biological molecule of interest, preferably a protein of interest, in a sample comprising compartments enclosed by at least one membrane, comprising the steps of:

fusing a photoactive yellow protein (PYP) functional derivative, or a functional fragment thereof, to the biological molecule of interest, thereby tagging the biological molecule of interest with the photoactive yellow protein (PYP) functional derivative, or a functional fragment thereof;

contacting the sample with a membrane-impermeant fluorogenic chromophore of formula (II) as previously described or a salt thereof; and detecting a fluorescence resulting from the binding of the membrane-impermeant fluorogenic chromophore of formula (II) to the photoactive yellow protein (PYP) functional derivative, or a functional fragment thereof;

thereby detecting the biological molecule of interest present at least in part at the extra membranous surface of the compartments, or secreted from the compartments, through the binding of the membrane-impermeant fluorogenic chromophore of formula (II) to the photoactive yellow protein (PYP) functional derivative, or a functional fragment thereof.

According to an embodiment, the biological molecule of interest is a membrane protein with at least a part of said protein extruding on the outside of said membrane or a secreted protein.

According to an embodiment, the binding of the membrane-impermeant fluorogenic chromophore to the photoactive yellow protein (PYP) functional derivative, or a functional fragment thereof, is reversible.

According to an embodiment, the method further comprises a step of quantifying the biological molecule of interest by measuring the fluorescence emitted upon binding of the membrane-impermeant fluorogenic chromophore of formula (II) to the photoactive yellow protein (PYP) functional derivative, or a functional fragment thereof, tagged to the biological molecule of interest.

This invention further relates to a method for sequentially labeling a protein of interest in a sample comprising compartments enclosed by at least one membrane, said method comprising:

fusing a photoactive yellow protein (PYP) functional derivative, or a functional fragment thereof, to the protein of interest, thereby tagging the protein of interest with the PYP functional derivative, or a functional fragment thereof;

contacting the sample with a membrane-impermeant fluorogenic chromophore of formula (II) as previously described or a salt thereof;

detecting a fluorescence resulting from the binding of the membrane-impermeant fluorogenic chromophore of formula (II) to the PYP functional derivative, or a functional fragment thereof, thereby detecting the fraction of protein of interest present at least in part at the extra membranous surface of the compartment or secreted from said compartment;

contacting the sample with a membrane-permeant fluorogenic chromophore able to specifically bind to the protein of interest;

detecting a fluorescence resulting from the binding of the membrane-permeant fluorogenic chromophore to the protein of interest, thereby detecting the whole population of protein of interest.

This invention further relates to an assay relying on the detection of a reporter protein in a sample comprising compartments enclosed by at least one membrane, said assay comprising the steps of:

obtaining a tagged reporter protein, wherein the reporter protein is tagged with a photoactive yellow protein (PYP) functional derivative, or a functional fragment thereof;

contacting the sample with a membrane-impermeant fluorogenic chromophore of formula (II) as previously described or a salt thereof; and detecting a fluorescence resulting from the binding of the membrane-impermeant fluorogenic chromophore of formula (II) to the PYP functional derivative, or a functional fragment thereof;

thereby detecting the reporter protein present at least in part at the extra membranous surface of the compartments, or secreted from the compartments, through the binding of the membrane-impermeant fluorogenic chromophore of formula (II) to the PYP functional derivative, or a functional fragment thereof.

According to an embodiment, the assay is for assessing the activity of a protein of interest involved in the expression or the anchoring of a reporter protein at the membrane or in the secretion of a reporter protein.

This invention further relates to a compound of formula (III):

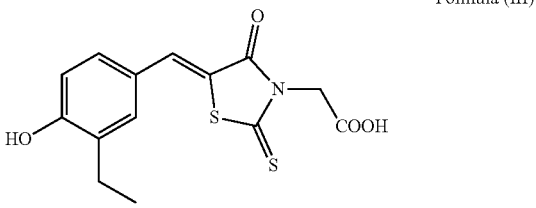

Formula (III)

or a salt thereof.

DETAILED DESCRIPTION

Figure 1:
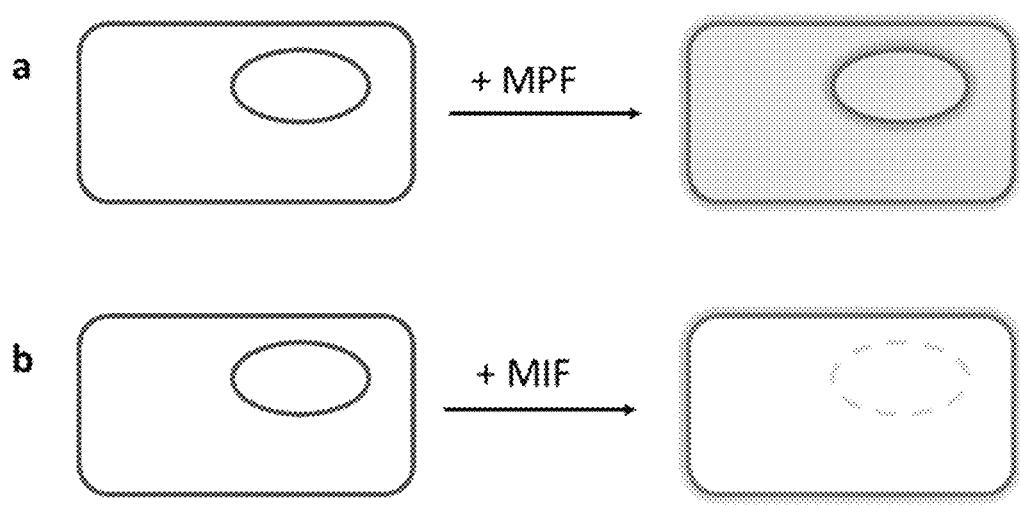
FIG. 1 is a drawing showing how membrane-impermeant fluorogens allow selective imaging of cell-surface FAST-tagged proteins in living cells. The cell (on the left) can be labeled by means of membrane-permeant fluorogens (MPF) as those existing in the art (a), of by membrane-impermeant fluorogens (MIF) according to the invention (b).

In the present invention, the following terms have the following meanings:

"About" preceding a figure means plus or less 10% of the value of said figure.

"Acid function" refers to a Brønsted acid, i.e. a group of atoms capable of donating a proton or hydrogen ion (H⁺).

"Basic function" refers to a Brønsted base, i.e. a group of atoms capable of receiving a proton or hydrogen ion (H⁺).

"Brightness" refers to the fluorescence output per emitter. It is equal to the product of the molar absorption coefficient (at the excitation wavelength) and the fluorescence quantum yield.

"Cell-surface protein" refers, in the present invention, to a protein present at least in part at the extracellular surface. In other words, according to the invention, a cell-surface protein extrudes at least in part from the cell membrane (also referred to as the plasma membrane). In an embodiment, a cell-surface protein is a membrane protein, such as a transmembrane protein or a protein anchored at the cell membrane, with at least one extracellular domain. In an embodiment, a cell-surface protein is protein present at the extracellular surface of the cell membrane.

"Chromophore" refers to a molecule which absorbs light at a specific wavelength and is thus colored.

"Compartment enclosed by at least one membrane" refers, in the present invention, to any closed entity that is delimited by a biological membrane consisting of a polar lipid layer, preferably a polar lipid bilayer. Examples of compartment enclosed by at least one membrane include, without being limited to, cells, vesicles, and artificial plasma membrane mimicking vesicles.

"Complex" within the context of the present invention, refers to the non-covalent or covalent, preferably non-covalent, association of a polypeptide, preferably a PYP polypeptide, with an organic molecule or salt from an organic molecule, preferably a fluorogenic chromophore.

"Derivative" of a protein refers to a fragment or to a variant of said protein.

"Extra membranous surface", within the context of the present invention, refers to the external or outward surface of a membrane enclosing a compartment, such as for example, a cell, a vesicle or an artificial plasma membrane mimicking vesicle. Thus, according to the present invention, the extra membranous surface of a compartment enclosed by at least one membrane refers to the surface of the membrane outside of said compartment. Accordingly, a biological molecule present at the extra membranous surface (of a compartment enclosed by at least one membrane), is a biological molecule present at least in part at the external surface of said membrane, i.e., a biological molecule present at least in part on the outside of said compartment enclosed by at least one membrane.

"Fluorogenic chromophore", within the context of the present invention, refers to a chromophore, the brightness of which can be significantly enhanced by an environmental change. The fluorogenic chromophore of the invention is substantially non-fluorescent in solution under its free form, but brightens up when placed into an environment constraining its conformation and excluding the non-fluorescent deexcitation of its excited state. In a particular embodiment of the invention, the free dye (i.e. the fluorogenic chromophore) is almost invisible in solution and becomes fluorescent upon binding of a protein scaffold which encases said fluorogenic chromophore in a cavity of the protein.

"Fluorescence quantum yield" represented by "ϕ" refers to the ratio of the number of photons emitted to the number of photons absorbed by a fluorogenic chromophore.

"Fluorophore" refers to a fluorescent chemical compound that can re-emit light upon light excitation.

"Peptide" refers to a linear polymer of amino acids of less than 50 amino acids linked together by peptide bonds. Moreover, the terms "protein" and "polypeptide" may be used interchangeably, unless otherwise specified. In one embodiment, a "polypeptide" refers to a linear polymer of at least 50 amino acids linked together by peptide bonds; and a "protein" specifically refers to a functional entity formed of one or more peptides or polypeptides, and optionally of non-polypeptides cofactors.

"Physiological pH" refers to a pH of about 7 to about 7.6, preferably about 7.4 measured in aqueous medium.

"Membrane" refers to a biological membrane, consisting of a polar lipid layer, preferably a polar lipid bilayer. According to the present invention, biological membranes include prokaryotic or eukaryotic cell membranes, vesicle membranes, artificial vesicle membranes. Cell membranes, thus include without being limited to, membranes of animal cells, plant cells, fungi, yeasts and bacteria.

"Membrane-impermeant" refers to a property of a compound which is not able to cross a membrane.

"Membrane-permeant" refers to a property of a compound which is able to cross a membrane.

"Molar absorption coefficient" represented by "ε" refers to a measurement of how strongly a chemical species absorbs light at a given wavelength.

"Reporter protein" refers to a protein which may be detected, localized or quantified as a way to indirectly assess a target or mechanism of interest, such as, for example, the activity of another protein, the interaction between proteins, protein internalization or protein secretion.

"Sample" refers to a specimen or small quantity of material, generally solid or liquid, comprising at least one biological molecule of interest and at least one membrane. "Sample" may also refer to cells or tissues or organisms of interest.

"Secreted protein" refers to a protein initially present within a cell, or a compartment enclosed by at least one membrane, that is excreted, i.e. that leaves said cell or said compartment.

"Alkoxy" refers to any O-alkyl group. Examples of alkoxy groups are methoxy, ethoxy, propoxy, butoxy or dodecoxy.

"Amido" refers to the —NR—COR' function wherein R may be —H or an alkyl group and wherein R' is an alkyl group.

"Amino" refers to a —NH$_2$ group or any group derived thereof by substitution of one or two hydrogen atoms by an organic aliphatic or aromatic group. Preferably, groups derived from —NH$_2$ are alkylamino groups, i.e. N-alkyl groups, comprising monoalkylamino and dialkylamino. According to a specific embodiment, the term "amino" refers to —NH$_2$, —NHMe or —NMe$_2$.

"Aryl" refers to a polyunsaturated, aromatic hydrocarbyl group having a single ring (i.e. phenyl) or multiple aromatic rings fused together (e.g. naphtyl) or linked covalently, typically containing 5 to 12 atoms, preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Alkyl" refers to a hydrocarbyl radical of formula $C_nH_{2n+1}$ wherein n is a number greater than or equal to 1. Typically, alkyl groups of this invention comprise from 1 to 12 carbon atoms, preferably from 1 to 6 carbon atoms. Alkyl groups may be linear or branched and may be substituted as indicated herein. Suitable alkyl groups include methyl, ethyl, propyl (n-propyl, i-propyl, n-butyl), butyl (i-butyl, s-butyl and t-butyl), pentyl and its isomers (e.g. n-pentyl, iso-pentyl), and hexyl and its isomers (e.g. n-hexyl, iso-hexyl).

"Carboxamide" refers to the —CO—NR function wherein R may be —H or an alkyl group.

"Carboxy" refers to the —COOH function, including —COO$^-$ and salts thereof.

"Carboxyalkyl" refers to any alkyl group substituted by one or more carboxy group. Examples of carboxyalkyl groups are carboxymethyl (—CH$_2$COOH) and carboxyethyl (—CH$_2$CH$_2$COOH) groups.

"Cyano" refers to the —C≡N function.

"Cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl.

"Halo" refers to fluoro, chloro, bromo or iodo. Preferred halo groups are fluoro and chloro.

"Haloalkyl" refers to any alkyl group substituted by one or more halo group. Examples of preferred haloalkyl groups are CF$_3$, CHF$_2$ and CH$_2$F.

"Haloalkoxy" refers to any alkoxy group substituted by one or more halo group.

"Hydroxyl" refers to the —OH function.

"Heteroalkyl" refers to alkyl group having at least one atom that is not carbon or hydrogen; preferably, said atom is selected from N, S, P and O. For example, a heteroalkyl can be an alkoxy group.

"Heterocycloalkyl" refers to a cycloalkyl group having at least one atom that is not carbon or hydrogen; preferably, said atom is selected from N, S, P and O.

"Hydrogen", when referring to a group, refers to a hydrogen atom (H).

"Nitro" refers to the —NO$_2$ function.

"Oxo" refers to the —C=O function.

"HBR" means "4-hydroxybenzylidene-rhodanine".

"HMBR" means "4-hydroxy-3-methylbenzylidene-rhodanine".

"n.d." means "not determined".

"PYP" means "Photoactive Yellow Protein".

This invention relates to 4-hydroxybenzylidene-rhodanine (HBR) analogs useful as membrane-impermeant fluorogenic chromophores.

According to an embodiment, the HBR analog is a compound of formula (I):

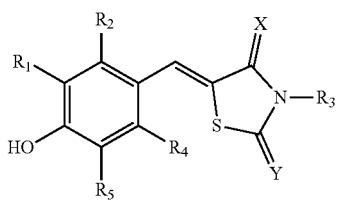

Formula (I)

wherein $R_1$, $R_2$, $R_4$ and $R_5$ may be identical or different and each represents hydrogen, halo, hydroxyl, aryl, alkyl, cycloalkyl, heteroalkyl or heterocycloalkyl group; said groups being saturated or unsaturated; optionally substituted by at least one group selected from halo, hydroxyl, oxo, nitro, amido, carboxy, amino, cyano, carboxamide haloalkoxy and haloalkyl;

$R_3$ represents hydrogen, hydroxyl, amino, aryl, alkyl, cycloalkyl, heteroalkyl or heterocycloalkyl group; saturated or unsaturated; optionally substituted by at least one group selected from halo, hydroxyl, oxo, nitro, amido, carboxy, carboxamide, amino, cyano, haloalkoxy, and haloalkyl; and X and Y may be identical or different and each represents O, S or N—$R_N$, wherein $R_N$ is hydrogen, aryl, alkyl, cycloalkyl, heteroalkyl or heterocycloalkyl group;

or a salt thereof.

In an embodiment, $R_1$, $R_2$, $R_4$ and $R_5$ do not simultaneously represent hydrogen atoms, i.e. are not all identical while at least one among $R_1$, $R_2$, $R_4$ and $R_5$ represents hydrogen.

In an embodiment, $R_1$, $R_2$, $R_4$ and $R_5$ may be identical or different and each represents hydrogen, halo, hydroxyl, alkyl or alkoxy group; saturated or unsaturated; optionally substituted by at least one group selected from halo, hydroxyl, oxo, nitro, amido, carboxy, amino and cyano. In a particular embodiment, $R_1$, $R_2$, $R_4$ and $R_5$ may be identical or different and each represents hydrogen, alkyl or alkoxy group. In a particular embodiment, the alkyl part of the alkyl or alkoxy groups comprises from 2 to 6 carbon atoms, preferably from 2 to 4 carbon atoms, more preferably 2 or 3 carbon atoms.

In an embodiment, $R_3$ is a charged group, i.e. a group bearing at least one charge at pH ranging from 6 to 8 in aqueous medium, for example at physiological pH (about 7.4 in aqueous medium). In an embodiment, $R_3$ comprises a positively charged group, for example a quaternary ammonium group. In an embodiment, $R_3$ comprises a basic function, for example a primary, secondary or tertiary amine. In a particular embodiment, the basic function has a $pK_A$ higher than 8, preferably higher than 9. In an embodiment, $R_3$ comprises an acid function. In a particular embodiment, the acid function has a $pK_A$ lower than 6, preferably lower than 5. In a particular embodiment, $R_3$ comprises at least one carboxy function. In a more particular embodiment, $R_3$ comprises a carboxy function having a $pK_A$ lower than 5, preferably about 4.

In an embodiment, $R_3$ represents a carboxyalkyl group. In a particular embodiment, $R_3$ comprises exactly one carboxy substituent. In a particular embodiment, $R_3$ is carboxymethyl group (—$CH_2COOH$).

The compounds of the invention may be in the form of salts. Salts of the compounds of the invention include the acid addition and base salts thereof.

Suitable acid addition salts are formed from a compound of the invention and at least one acid. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts.

Suitable base salts are formed from a compound of the invention and at least one base. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts.

Hemisalts of acids and bases may also be formed, for example, hemisulphate and hemicalcium salts. When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Salts of compounds of the invention may be prepared by one or more of these methods: (i) by reacting the compound of the invention with the desired acid; (ii) by reacting the compound of the invention with the desired base; (iii) by removing an acid- or base-labile protecting group from a suitable precursor of the compound of the invention or by ring-opening a suitable cyclic precursor, for example, a lactone or lactam, using the desired acid; or (iv) by converting one salt of the compound of the invention to another by reaction with an appropriate acid or by means of a suitable ion exchange column.

In an embodiment, the HBR analog is a compound of formula (II):

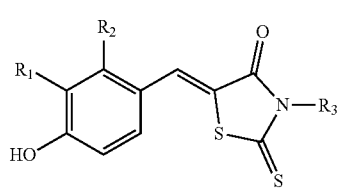

Formula (II)

wherein $R_1$ represents hydrogen, alkyl group having at least 2 carbon atoms or alkoxy group having at least 2 carbon atoms;

$R_2$ represents hydrogen, alkyl group or alkoxy group; and $R_3$ represents carboxyalkyl group;

or a salt thereof.

In a particular embodiment, $R_1$ represents alkyl group or alkoxy group, wherein the alkyl part of the group comprises from 2 to 6 carbon atoms, preferably from 2 to 4 carbon atoms, more preferably 2 or 3 carbon atoms. In a more particular embodiment, $R_1$ represents ethyl (—$CH_2CH_3$) or ethoxy (—$OCH_2CH_3$) group.

In a particular embodiment, $R_2$ represents alkyl group or alkoxy group, wherein the alkyl part of the group comprises from 1 to 6 carbon atoms, preferably from 1 to 4 carbon atoms, more preferably 1 or 2 carbon atoms. In a more particular embodiment, $R_2$ represents methoxy (—$OCH_3$) group. In another particular embodiment, $R_2$ represents alkyl group or alkoxy group, wherein the alkyl part of the group comprises from 2 to 6 carbon atoms, preferably from 2 to 4 carbon atoms, more preferably 2 or 3 carbon atoms.

In a particular embodiment, at least one among $R_1$ and $R_2$ represent hydrogen. In a particular embodiment, $R_1$ and $R_2$ are different. In a more particular embodiment, either $R_1$ or $R_2$ represents hydrogen. In a more particular embodiment, one of $R_1$ and $R_2$ represents hydrogen while the other represents an alkyl or alkoxy group.

In a particular embodiment, $R_3$ represents carboxyalkyl group wherein the alkyl part of the group comprises from 1 to 6 carbon atoms, preferably from 1 to 3 carbon atoms, more preferably 1 or 2 carbon atoms, furthermore preferably 1 carbon atom. In a more particular embodiment, $R_3$ represents carboxyalkyl group wherein the alkyl part of the group comprises exactly one carbon atom. In a particular embodiment, $R_3$ comprises exactly one carboxy group. In a more particular embodiment, $R_3$ is carboxymethyl group (—$CH_2COOH$).

In a particular embodiment, the compound of formula (II) is selected from:
(Z)-2-(5-(4-hydroxy-2-methoxybenzylidene)-4-oxo-2-thioxothiazolidin-3-yl)acetic acid [HBRAA-2OM];
(Z)-2-(5-(4-hydroxy-3-ethylbenzylidene)-4-oxo-2-thioxothiazolidin-3-yl)acetic acid [HBRAA-3E]; and
(Z)-2-(5-(4-hydroxy-3-ethoxybenzylidene)-4-oxo-2-thioxothiazolidin-3-yl)acetic acid [HBRAA-3OE].

In a more particular embodiment, HBR analog is (Z)-2-(5-(4-hydroxy-3-ethylbenzylidene)-4-oxo-2-thioxothiazolidin-3-yl)acetic acid [HBRAA-3E], i.e. a compound of formula (III):

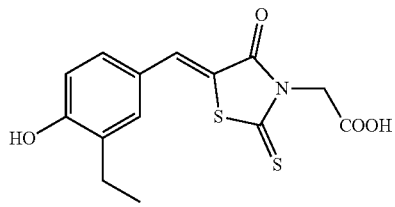

Formula (III)

or salt thereof.

HBR analogs may be manufactured by suitable methods known of a person skilled in the art. According to an embodiment, the HBR analog according to the invention is synthesized by the reaction of rhodamine-3-acetic acid with a substituted 4-hydroxy-benzaldehyde. Substituted 4-hydroxy-benzaldehyde can be prepared by suitable methods well-known of a person skilled in the art, for example by aromatic formylation of a substituted phenol.

In an embodiment, the compound of formula (I), and subformulae thereof, is for use as membrane-impermeant fluorogenic chromophore.

In a particular embodiment, the compound of formula (I), and subformulae thereof, is for use in binding reversibly a photoactive yellow protein (PYP) functional derivative, or a functional fragment thereof.

The invention further relates to a complex formed by a 4-hydroxybenzylidene-rhodanine (HBR) analog according to the invention with a photoactive yellow protein (PYP) functional derivative, or a functional fragment thereof.

"Photoactive yellow protein" or "PYP" is a photoreceptor protein isolated, for instance, from purple photosynthetic bacteria *Ectothiorhodospira halophila* (*Halorhodospira halophila*). The wild-type PYP is a relatively small protein (14 kDa), which can bind p-coumaric acid, a chromophore, through a thioester bond at the 69th cysteine residue.

According to the present invention, the photoactive yellow protein (PYP) functional derivative, or a functional fragment thereof, is capable of binding the membrane-impermeant 4-hydroxybenzylidene-rhodanine (HBR) analog of the invention.

According to an embodiment, the photoactive yellow protein (PYP) functional derivative, or a functional fragment thereof, binds the HBR analog of the invention reversibly, i.e. through non-covalent interactions. Thus, according to an embodiment, the binding of the membrane-impermeant fluorogenic chromophore of the invention to the photoactive yellow protein (PYP) functional derivative, or a functional fragment thereof, is reversible.

Methods for assessing the binding of a fluorogenic chromophore to a polypeptide are well-known in the art. Such methods may notably rely on the assessment of the fluorescence emitted by the chromophore upon binding to the polypeptide and include spectrofluorimetry. In an embodiment, fluorescence spectra are recorded with a spectrofluorimeter as described in the Examples. According to an embodiment, the photoactive yellow protein (PYP) functional derivative, or a functional fragment thereof, binds the HBR analog of the invention with a $K_D$ lower than about 20 µM, preferably lower than 15 µM, more preferably lower than 10 µM when measured at a temperature of about 25° C. In an embodiment, the $K_D$ is lower than about 7 µM, about 6 µM, or about 5 µM at about 25° C. In a particular embodiment, the $K_D$ is lower than about 3 µM, about 2.5 µM or about 2 µM at about 25° C.

Methods for measuring the thermodynamic dissociation constant $K_D$ are well-known in the art, and include, for example, those described by Plamont, M.-A. et al., (Plamont, M.-A. et al., *P Natl Acad Sci Usa* 2016, 113 (3), 497). In an embodiment, the thermodynamic dissociation constant $K_D$ is determined by spectrofluorometric titration as described in the Examples.

According to an embodiment, the photoactive yellow protein (PYP) functional derivative, or a functional fragment thereof, enhances the brightness of the HBR analog of the invention through the motion restriction thereof. In an embodiment, the brightness of the HBR analog of the invention is enhanced through the motion restriction thereof.

According to an embodiment, the molar absorption coefficient ($\varepsilon$) of the complex of the invention ranges from about 10 to about 100 mM$^{-1}$cm$^{-1}$ when measured at its wavelength of maximal absorption ($\lambda_{abs}$). In an embodiment, the molar absorption coefficient ($\varepsilon$) ranges from about 40 to about 80 mM$^{-1}$cm$^{-1}$ at $\lambda_{abs}$. In a particular embodiment, the molar absorption coefficient ($\varepsilon$) ranges from about 55 to about 65 mM$^{-1}$cm$^{-1}$ at $\lambda_{abs}$.

Methods for measuring the molar absorption coefficient ($\varepsilon$) are known in the art, and include, for example, those described by Plamont, M.-A. et al., (Plamont, M.-A. et al., *P Natl Acad Sci Usa* 2016, 113 (3), 497).

According to an embodiment, the fluorescence quantum yield ($\phi$) of the complex of the invention is greater than about 0.2% when measured at its wavelength of maximal absorption ($\lambda_{abs}$). In an embodiment, φ is greater than about 1%, about 2%, or about 3% at $\lambda_{abs}$. In a particular embodiment, φ is greater than about 5% at $\lambda_{abs}$.

Methods for measuring the fluorescence quantum yield (φ) are known in the art, and include, for example, those described by Plamont, M.-A. et al., 2016. In an embodiment, the fluorescence quantum yields after one-photon excitation φ are calculated from the relation:

$$\phi = \phi_{ref} \frac{1-10^{-A_{ref}(\lambda_{exc})}}{1-10^{-A(\lambda_{exc})}} \frac{D}{D_{ref}} \left(\frac{n}{n_{ref}}\right)^2$$

where the subscript ref stands for standard samples. $A(\lambda_{exc})$ is the absorbance at the excitation wavelength $\lambda_{exc}$, D is the integrated emission spectrum, and n is the refractive index for the solvent.

According to an embodiment, the brightness of the complex of the invention is greater than about 60. In an embodiment, the brightness is greater than about 400. In a particular embodiment, the brightness is greater than about 2,500.

Methods for measuring the brightness are well-known in the art. Brightness corresponds to the fluorescence output per emitter and is the product of the molar absorption coefficient (at the excitation wavelength) and the fluorescence quantum yield.

According to an embodiment, the photoactive yellow protein (PYP) functional derivative, or a functional fragment thereof, induces a spectral shift of the HBR analog of the invention. In an embodiment, the spectral shift of the HBR analog of the invention is induced through the ionization of an auxochromic group thereof.

According to an embodiment, the photoactive yellow protein (PYP) functional derivative, or a functional fragment thereof, derives from a PYP of a species selected from the group consisting of *Halorhodospira halophila* (PYP of SEQ ID NO: 49), *Halomonas boliviensis* LC1 (PYP of SEQ ID NO: 50), *Halomonas* sp. GFAJ-1 (PYP of SEQ ID NO: 51), *Rheinheimera* sp. A13L (PYP of SEQ ID NO: 52), *Iodomarina loihiensis* (PYP of SEQ ID NO: 53), *Thiorhodospira sibirica* ATCC 700588 (PYP of SEQ ID NO: 54), *Rhodothalassium salexigens* (PYP of SEQ ID NO: 55), *Roseomonas cervicalis* ATCC 49957 (PYP of SEQ ID NO: 56), *Rhodobacter sphaeroides* (PYP of SEQ ID NO: 57), *Leptospira wolbachii* (PYP of SEQ ID NO: 58), *Rhodobacter capsulatus* (PYP of SEQ ID NO: 59), *Rhodospirillum centenum* (PYP of SEQ ID NO: 60), *Leptospira vanthielii* (PYP of SEQ ID NO: 61), *Leptospira terpstrae* (PYP of SEQ ID NO: 62), *Leptospira biflexa* serovar Patoc strain "Patoc 1 (Paris)" (PYP of SEQ ID NO: 63), *Leptospira meyeri* (PYP of SEQ ID NO: 64), *Leptospira yanagawae* (PYP of SEQ ID NO: 65), *Salinibacter ruber* DSM 13855 (PYP of SEQ ID NO: 66), *Burkholderia phytofirmans* PsJN (PYP of SEQ ID NO: 67), *Phaeospirillum fulvum* (PYP of SEQ ID NO: 68), *Acidithiobacillus thiooxidans* (PYP of SEQ ID NO: 69), *Acidithiobacillus caldus* SM-1 (PYP of SEQ ID NO: 70), *Gamma proteobacterium* NOR5-3 (PYP of SEQ ID NO: 71), *Methylotenera versatilis* 301 (PYP of SEQ ID NO: 72), *Leptothrix cholodnii* SP-6 (PYP of SEQ ID NO: 73), *Caenispirillum salinarum* (PYP of SEQ ID NO: 74), *Stigmatella aurantiaca* DW4/3-1 (PYP of SEQ ID NO: 75), *Massilia timonae* (PYP of SEQ ID NO: 76), *Methyloversatilis universalis* FAM 5 (PYP of SEQ ID NO: 77), *Spirosoma linguale* DSM 74 (PYP of SEQ ID NO: 78), *Rhodopseudomonas palstris* BisB5 (PYP of SEQ ID NO: 79), *Sorangium cellulosum* "So ce 56" (PYP of SEQ ID NO: 80) and *Rhodomicrobium vannielii* ATCC 17100 (PYP of SEQ ID NO: 81).

In a particular embodiment, the photoactive yellow protein (PYP) functional derivative, or a functional fragment thereof, derives from a PYP having the sequence of SEQ ID NO: 48, corresponding to the PYP of *Halorhodospira halophila* with the mutation C69G.

Within the present invention, by "functional PYP derivative", it is meant a PYP polypeptide that is capable of binding to an HBR analog according to the invention. According to an embodiment, the functional PYP derivative thus has the capacity of specifically and reversibly binding the HBR analog according to the invention.

According to an embodiment, the PYP functional derivative, or a functional fragment thereof, binding to the HBR analog according to the invention is a variant of a PYP.

In an embodiment, a variant of a PYP is an amino acid sequence comprising at least 8, preferably at least 10, 20 50, 100, or 125 contiguous amino acids of a PYP, for example of a PYP having the sequence of SEQ ID NO: 48.

In an embodiment, a variant of a PYP is a peptide or a polypeptide comprising at least 8, preferably at least 10, 20, 50, 100, or 125 contiguous amino acids of a PYP, for example of a PYP having the sequence of SEQ ID NO: 48.

In an embodiment, a variant of a PYP is a peptide or polypeptide having at least 30%, 35%, 40%, 45%, 50%, 55%, 60%, 65%, 70%, 75%, 80%, 90%, or 95%, or at least 96%, 97%, 98%, or 99% identity with the amino acid sequence of a PYP or a fragment thereof, for example of a PYP having the sequence of SEQ ID NO: 48 or a fragment thereof.

According to an embodiment, a PYP variant as described above retains the ability to bind specifically the above disclosed HBR analog.

The term "identity" or "identical", when used in a relationship between the sequences of two or more peptides or polypeptides, refers to the degree of sequence relatedness between peptides or polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides or polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al., NCB/NLM/NIH Bethesda, Md. 20894; Altschul et al., supra). The well-known Smith Waterman algorithm may also be used to determine identity.

Within the present invention, by "functional fragment", it is meant an incomplete PYP or an incomplete PYP functional derivative which has retained its ability to bind specifically the above disclosed HBR analog. According to an embodiment, a functional fragment of PYP thus has the capacity of specifically and reversibly binding the HBR analog according to the invention.

In an embodiment, a functional fragment is an amino acid sequence of at least 8 amino acids (preferably contiguous amino acids), preferably of at least 10, 15, 20, 25, 30, 40, 50, 60, 70, 80, 90, 100, 110, or 120 amino acids (preferably contiguous amino acids).

In an embodiment, a functional fragment of a PYP is an amino acid sequence of at least 8, preferably of at least 10, 15, 20, 25, 30, 40, 50, 60, 70, 80, 90, 100, 110, or 120 amino acids (preferably contiguous amino acids) of a PYP, for example of a PYP having the sequence of SEQ ID NO: 48.

In an embodiment, a functional fragment of a PYP or of a variant thereof comprises amino acids 70-125, 80-120, 90-110 or 94-101 of a PYP (wherein the numbering of the amino acid sequences is made by reference to the sequence of SEQ ID NO: 48), for example of a PYP having the sequence of SEQ ID NO: 48.

In an embodiment, a fragment of PYP or of a variant thereof comprises amino acids 1-101, 10-101, 20-101, 30-101, 40-101, 50-101, 60-101, 70-101, 80-101, 90-101, 90-110, 90-120 or 90-125 of a PYP (wherein the numbering of the amino acid sequences is made by reference to the sequence of SEQ ID NO: 48), for example of a PYP having the sequence of SEQ ID NO: 48.

In an embodiment, the PYP functional derivative, or a functional fragment thereof, binding to an HBR analog according to the invention comprises or consists of a polypeptide selected in the group consisting of SEQ ID NO: 48-81, or a functional fragment thereof, further comprising at least one, preferably at least two, preferably at least three, preferably at least four, preferably all of the modifications selected in the group consisting of:
  an amino acid substitution by a proline at position 97;
  an amino acid substitution by a tryptophan at position 94;
  an amino acid substitution by an amino acid residue with branched aliphatic side chain, preferably isoleucine, valine or leucine, at position 96; and/or
  an amino acid substitution by a threonine at position 98;
  wherein the numbering of the amino acid sequences is made by reference to the sequence of SEQ ID NO: 48.

In an embodiment, the PYP functional derivative, or a functional fragment thereof, binding to an HBR analog according to the invention comprises or consists of a polypeptide having at least 30%, 35%, 40%, 45%, 50%, 55%, 60%, 65%, 70%, 75%, 80%, 90%, or 95% identity with a sequence selected in the group consisting of SEQ ID NO: 48-81, preferably with SEQ ID NO: 48, or a functional fragment thereof, further comprising at least one, preferably at least two, preferably at least three, preferably at least four, preferably all of the modifications selected in the group consisting of:
  an amino acid substitution by a proline at position 97;
  an amino acid substitution by a tryptophan at position 94;
  an amino acid substitution by an amino acid residue with branched aliphatic side chain, preferably isoleucine, valine or leucine, at position 96; and/or
  an amino acid substitution by a threonine at position 98;
  wherein the numbering of the amino acid sequences is made by reference to the sequence of SEQ ID NO: 48.

In an embodiment, the PYP functional derivative, or a functional fragment thereof, binding to an HBR analog according to the invention comprises or consists of a polypeptide having a sequence selected in the group consisting of SEQ ID NO: 48-81 or a functional fragment thereof, or a sequence having at least 30%, 35%, 40%, 45%, 50%, 55%, 60%, 65%, 70%, 75%, 80%, 90%, or 95% identity with a sequence selected in the group consisting of SEQ ID NO: 48-81, preferably SEQ ID NO: 48, or a functional fragment thereof, further comprising at least one, preferably at least two, preferably at least three, preferably at least four, preferably all of the modifications selected in the group consisting of:
  an amino acid substitution by a proline at position 97;
  an amino acid substitution by a tryptophan at position 94;
  an amino acid substitution by an amino acid residue with branched aliphatic side chain, preferably isoleucine, valine or leucine, at position 96; and/or
  an amino acid substitution by a threonine at position 98;
  wherein the numbering of the amino acid sequences is made by reference to the sequence of SEQ ID NO: 48.

Amino acid 94 in SEQ ID NO: 48 corresponds to amino acid 94 in SEQ ID NO: 49, 50-55, 68, 70, 77 and 79; to amino acid 93 in SEQ ID NO: 56, 57, and 59; to amino acid 92 in SEQ ID NO: 73 and 76; to amino acid 89 in SEQ ID NO: 62-65 and 69; to amino acid 95 in SEQ ID NO: 72 and 75; to amino acid 90 in SEQ ID NO: 74; to amino acid 91 in SEQ ID NO: 66 and 81; to amino acid 83 in SEQ ID NO: 58 and 61; to amino acid 87 in SEQ ID NO: 60 and 78; to amino acid 77 in SEQ ID NO: 67 and 80; and to amino acid 78 in SEQ ID NO: 71.

Amino acid 96 in SEQ ID NO: 48 corresponds to amino acid 96 in SEQ ID NO: 49, 50-55, 68, 70, 77 and 79; to amino acid 95 in SEQ ID NO: 56, 57, and 59; to amino acid 94 in SEQ ID NO: 73 and 76; to amino acid 91 in SEQ ID NO: 62-65 and 69; to amino acid 97 in SEQ ID NO: 72 and 75; to amino acid 92 in SEQ ID NO: 74; to amino acid 93 in SEQ ID NO: 66 and 81; to amino acid 85 in SEQ ID NO: 58 and 61; to amino acid 89 in SEQ ID NO: 60 and 78; to amino acid 79 in SEQ ID NO: 67 and 80; and to amino acid 80 in SEQ ID NO: 71.

Amino acid 97 in SEQ ID NO: 48 corresponds to amino acid 97 in SEQ ID NO: 49, 50-55, 68, 70, 77 and 79; to amino acid 96 in SEQ ID NO: 56, 57, and 59; to amino acid 95 in SEQ ID NO: 73 and 76; to amino acid 92 in SEQ ID NO: 62-65 and 69; to amino acid 98 in SEQ ID NO: 72 and 75; to amino acid 93 in SEQ ID NO: 74; to amino acid 94 in SEQ ID NO: 66 and 81; to amino acid 86 in SEQ ID NO: 58 and 61; to amino acid 90 in SEQ ID NO: 60 and 78; to amino acid 80 in SEQ ID NO: 67 and 80; and to amino acid 91 in SEQ ID NO: 71.

Amino acid 98 in SEQ ID NO: 48 corresponds to amino acid 98 in SEQ ID NO: 49, 50-55, 68, 70, 77 and 79; to amino acid 97 in SEQ ID NO: 56, 57, and 59; to amino acid 96 in SEQ ID NO: 73 and 76; to amino acid 93 in SEQ ID NO: 62-65 and 69; to amino acid 99 in SEQ ID NO: 72 and 75; to amino acid 94 in SEQ ID NO: 74; to amino acid 95 in SEQ ID NO: 66 and 81; to amino acid 87 in SEQ ID NO: 58 and 61; to amino acid 91 in SEQ ID NO: 60 and 78; to amino acid 81 in SEQ ID NO: 67 and 80; and to amino acid 82 in SEQ ID NO: 71.

In an embodiment, the PYP functional derivative, or a functional fragment thereof, binding to an HBR analog according to the invention comprises an amino acid sequence at position 94-101, by reference to the sequence of SEQ ID NO: 48, having the following sequence: WX$_1$IPTX$_2$X$_3$X$_4$ (SEQ ID NO: 129), wherein X$_1$, X$_2$, X$_3$ and X$_4$ each independently are any amino acid. In an embodiment, the PYP functional derivative, or a functional fragment thereof, binding to an HBR analog according to the invention comprises an amino acid sequence having the following sequence: WX$_1$IPTX$_2$X$_3$X$_4$ (SEQ ID NO: 129), wherein X$_1$, X$_2$, X$_3$ and X$_4$ each independently are any amino acid.

In a particular embodiment, the PYP functional derivative, or a functional fragment thereof, binding to an HBR analog according to the invention comprises an amino acid sequence at position 94-101, by reference to the sequence of SEQ ID NO: 48, selected in the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127 and SEQ ID NO: 128. In a particular embodiment, the PYP functional derivative, or a functional fragment thereof, binding to an HBR analog according to the invention comprises an amino acid selected in the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127 and SEQ ID NO: 128.

Preferably, the PYP functional derivative, or a functional fragment thereof, binding to an HBR analog according to the invention comprises an amino acid region at position 94-101 of SEQ ID NO: 83 with reference to SEQ ID NO: 48. In an embodiment, the PYP functional derivative, or a functional fragment thereof, binding to an HBR analog according to the invention comprises the amino acid sequence of SEQ ID NO: 83.

In a particular embodiment, the PYP functional derivative, or a functional fragment thereof, binding to an HBR analog according to the invention comprises or consists in a sequence selected in the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47, or a functional fragment thereof.

Preferably, the PYP functional derivative, or a functional fragment thereof, binding to an HBR analog according to the invention comprises or consists in SEQ ID NO: 3.

According to an embodiment, the PYP functional derivative, or a functional fragment thereof, binding to an HBR analog according to the invention can be expressed in fusion with any protein of interest within a host cell by inserting (for example via transformation or transfection) a nucleic acid sequence which encodes the resulting fusion protein.

According to an embodiment, the protein of interest is fused to a photoactive yellow protein (PYP) functional derivative, or a functional fragment thereof, as described above. According to an embodiment, the protein of interest is fused to a PYP functional derivative comprising or consisting in SEQ ID NO: 3. According to an embodiment, the protein of interest is fused to a PYP functional derivative comprising or consisting in SEQ ID NO: 83.

According to an embodiment, the protein of interest is tagged with a photoactive yellow protein (PYP) functional derivative, or a functional fragment thereof, as described above. According to an embodiment, the protein of interest is tagged with a PYP functional derivative comprising or consisting in SEQ ID NO: 3. According to an embodiment, the protein of interest is tagged with a PYP functional derivative comprising or consisting in SEQ ID NO: 83.

The invention also relates to a kit comprising a 4-hydroxybenzylidene-rhodanine (HBR) analog according to the invention and a vector comprising a nucleic acid sequence encoding a photoactive yellow protein (PYP) functional derivative, or a functional fragment thereof, as described above wherein a nucleic acid sequence encoding a protein of interest is to be inserted.

The invention further relates to the use of a 4-hydroxybenzylidene-rhodanine (HBR) analog according to the invention as membrane-impermeant fluorogenic chromophore.

According to an embodiment, the 4-hydroxybenzylidene-rhodanine (HBR) analog is of formula (I), formula (II) and/or formula (III).

According to an embodiment, the membrane-impermeant fluorogenic chromophore may be used in vitro and/or in vivo for biological research, such as, for example, research in molecular biology, cell biology, developmental biology, neurobiology, immunology or physiology.

According to an embodiment, the membrane-impermeant fluorogenic chromophore of the invention is used in combination with at least one other fluorogenic chromophore. In an embodiment, the at least one other fluorogenic chromophore emits in a different wavelength. In an embodiment, the at least one other fluorogenic chromophore is a membrane-impermeant fluorogenic chromophore. In an embodiment, the at least one other fluorogenic chromophore is a membrane-permeant fluorogenic chromophore, for example HBR or HMBR.

The present invention further relates to a method for detecting a biological molecule of interest in a sample comprising compartments enclosed by at least one membrane, said method comprising the steps of:
    fusing a photoactive yellow protein (PYP) functional derivative, or a functional fragment thereof, as described above to the biological molecule of interest, thereby tagging the biological molecule of interest with the PYP functional derivative, or a functional fragment thereof;

contacting the sample with a 4-hydroxybenzylidene-rhodanine (HBR) analog according to the invention; and detecting a fluorescence resulting from the binding of the HBR analog to the PYP functional derivative, or a functional fragment thereof;

thereby detecting the biological molecule of interest present at least in part at the extra membranous surface of the compartments, or secreted from the compartments, through the binding of the HBR analog to the PYP functional derivative, or a functional fragment thereof.

The present invention also relates to a method of detecting a biological molecule of interest in a sample comprising compartments enclosed by at least one membrane, said method comprising the steps of:

obtaining a tagged biological molecule of interest, wherein the biological molecule of interest is tagged with a photoactive yellow protein (PYP) functional derivative, or a functional fragment thereof, as described above; and contacting the sample with a 4-hydroxybenzylidene-rhodanine (HBR) analog according to the invention;

detecting a fluorescence resulting from the binding of the HBR analog to the PYP functional derivative, or a functional fragment thereof;

thereby detecting the biological molecule of interest present at least in part at the extra membranous surface of the compartments, or secreted from the compartments, through the binding of the HBR analog to the PYP functional derivative, or a functional fragment thereof.

According to the present invention, compartments enclosed by at least one membrane include, without being limited to, cells, vesicles, and artificial plasma membrane mimicking vesicles. Example of cells include, without being limited to, bacteria, yeasts, fungi, plant cells, animal or metazoan cells such as insect cells, mammal cells or human cells. Examples of vesicles include, without being limited to, cell organelles such as mitochondria, endoplasmic reticulum, Golgi apparatus, lysosomes, peroxisomes; cell nuclei; and microsomes.

In an embodiment, the compartments enclosed by at least one membrane are cells. Thus, according to an embodiment, the sample comprising compartments enclosed by at least one membrane is a cell sample, a cell culture, or a suspension of vesicles. In an embodiment, the sample comprising compartments enclosed by at least one membrane is a cell culture.

Examples of cell samples include, without being limited to, tissue samples and biopsies. Examples of cell cultures include, without being limited to, cultures of bacteria, cultures of yeasts, cultures of fungi, cultures of plan cells, cultures of animal cells such as cultures of insect cells, cultures of mammal cells, or cultures of human cells. Examples of suspensions of vesicles include, without being limited to, microsomal fractions obtained after centrifugation of cells.

According to an embodiment, said method of the invention is for detecting a biological molecule of interest in a sample comprising cells and allows the detection of the biological molecule of interest present at least in part at the extracellular surface, or secreted from the cells.

According to the present invention, the detection of fluorescence may be performed by any method known in the art, including epifluorescence microscopy, confocal microscopy, super-resolution microscopy, spectrofluorimetry, fluorescence correlation spectroscopy, and flow cytometry.

According to an embodiment, the biological molecule of interest is extracellular, i.e. is not inside of a cell. In an embodiment, the biological molecule of interest is located on the outward or external surface of a cell, a vesicle, or an artificial vesicle. In an embodiment, the biological molecule of interest is secreted from a cell or from a vesicle such as a microsome. In a particular embodiment, the biological molecule of interest is a membrane protein. In a particular embodiment, the biological molecule of interest is a cell-surface protein, present at least in part at the extra membranous surface.

According to an embodiment, the biological molecule of interest is a protein of interest. The protein of interest may be a natural protein, a chimeric protein resulting from the fusion of various protein domains or a synthetic protein. In an embodiment, the protein of interest is a membrane protein, a cell-surface protein, present at least in part at the extra membranous surface, or a secreted protein. In an embodiment, the protein of interest is a membrane protein with at least a part of said protein extruding on the outside of said membrane or a secreted protein.

Methods for fusing a peptide tag to a protein of interest are well-known and routinely used in research laboratories. Briefly, such methods comprise inserting the nucleic sequence encoding a protein of interest in a vector comprising the nucleic sequence encoding the tag. The nucleic sequence encoding the protein of interest can be inserted so that the tag is situated at the N terminus of the protein of interest or at the C terminus of the protein of interest, or internally, as desired. Additionally, a short nucleic sequence encoding a linker or spacer may be present between the nucleic sequence encoding the tag and the nucleic sequence encoding the protein of interest.

A vector comprising the nucleic acid sequence encoding the tagged protein of interest, i.e. the expression vector, is then inserted into a host cell, such as for example, by transformation or transfection, so that the tagged protein of interest is expressed by said host cell.

According to an embodiment, the present invention relates to a method for detecting a protein of interest fused to or tagged with a photoactive yellow protein (PYP) functional derivative, or a functional fragment thereof, as described above in a sample comprising compartments enclosed by at least one membrane, by contacting said sample with a 4-hydroxybenzylidene-rhodanine (HBR) analog according to the invention.

According to the present invention, the protein of interest is tagged with a photoactive yellow protein (PYP) functional derivative, or a functional fragment thereof, as described above wherein the PYP functional derivative, or a functional fragment thereof, tagged to the protein of interest is present on the external side of the membrane of the compartment, such as, for example, the cell or the vesicle, comprising the protein of interest.

In an embodiment, the protein of interest is tagged at its N terminus. In another embodiment, the protein of interest is tagged at its C terminus. In another embodiment, the protein of interest is tagged internally.

In an embodiment, the protein of interest is present at the surface of the compartment enclosed by at least one membrane and the protein of interest is tagged at its N terminus, at its C terminus, or in an internal domain, so that the tag is exposed on the outside of said compartment.

In an embodiment, the protein of interest is secreted and comprises a signal peptide that prompts the protein to translocate, usually the signal peptide is present at the N terminus of the protein. Accordingly, in an embodiment the protein of interest that is secreted and comprises a signal peptide is tagged on the extremity that does not comprise said signal peptide.

According to an embodiment, the method of the invention is an in vitro method.

According to an embodiment, the method of detecting the biological molecule of interest of the invention further comprises a step of quantifying the biological molecule of interest by measuring the fluorescence emitted upon binding of the HBR analog of the invention to the PYP functional derivative, or a functional fragment thereof, tagged to the biological molecule of interest.

According to the present invention, the measurement of fluorescence may be performed by any method known in the art, including spectrofluorimetry, fluorescence correlation spectroscopy, flow cytometry and analysis of images obtained by epifluorescence microscopy, confocal microscopy, or super-resolution microscopy.

According to an embodiment, the HBR analog of the invention is used in combination with at least one other fluorogenic chromophore. In an embodiment, the at least one other fluorogenic chromophore emits in a different wavelength. In an embodiment, the at least one other fluorogenic chromophore is a membrane-impermeant fluorogenic chromophore. In an embodiment, the at least one other fluorogenic chromophore is a membrane-permeant fluorogenic chromophore, for example HBR or HMBR.

The present invention also relates to a method for sequentially labeling a biological molecule of interest, in particular a protein of interest, in a sample comprising compartments enclosed by at least one membrane, said method comprising:
    fusing a photoactive yellow protein (PYP) functional derivative, or a functional fragment thereof, as described above to the biological molecule of interest, in particular to the protein of interest, thereby tagging the biological molecule of interest, in particular the protein of interest, with the PYP functional derivative, or a functional fragment thereof;
    contacting the sample with a membrane-impermeant 4-hydroxybenzylidene-rhodanine (HBR) analog according to the invention;
    detecting a fluorescence resulting from the binding of the HBR analog to the PYP functional derivative, or a functional fragment thereof, thereby detecting the fraction of biological molecule of interest, in particular of protein of interest, present at least in part at the extra membranous surface of the compartment, or secreted from said compartment;
    contacting the sample with a membrane-permeant fluorogenic chromophore able to specifically bind to the biological molecule of interest, in particular to the protein of interest;
    detecting a fluorescence resulting from the binding of the membrane-permeant fluorogenic chromophore to the biological molecule of interest, in particular to the protein of interest, thereby detecting the whole population of biological molecule of interest, in particular of protein of interest.

In an embodiment, the 4-hydroxybenzylidene-rhodanine (HBR) analog according to the invention and the membrane-permeant fluorogenic chromophore emit in different wavelengths. In an embodiment, the membrane-permeant fluorogenic chromophore binds to the PYP functional derivative, or a functional fragment thereof, as described above. Examples of such membrane-permeant fluorogenic chromophore include, for example, 4-hydroxybenzylidene rhodanine (HBR) and 4-hydroxy-3-methylbenzylidene rhodanine (HMBR).

According to an embodiment, said method of the invention is for sequentially labeling a biological molecule of interest, in particular a protein of interest, in a sample comprising cells and allows the detection of the fraction of biological molecule of interest, in particular of protein of interest, present at least in part at the extracellular surface, or secreted from the cells and the detection of the whole population of biological molecule of interest, in particular of protein of interest.

The present invention also relates to a method for quantifying, in a sample comprising compartments enclosed by at least one membrane, the fraction of a biological molecule of interest, in particular a protein of interest, that is present at least in part at the extra membranous surface of the compartments, or secreted from the compartments, with reference to the whole population of biological molecule of interest, in particular of protein of interest, said method comprising the steps of:
    obtaining a tagged biological molecule of interest, in particular a tagged protein of interest, wherein the biological molecule of interest, in particular the protein of interest, is tagged with a photoactive yellow protein (PYP) functional derivative, or a functional fragment thereof, as described above; and
    contacting the sample, either simultaneously or sequentially, with a 4-hydroxybenzylidene-rhodanine (HBR) analog according to the invention and with a membrane-permeant fluorogenic chromophore able to specifically bind to the biological molecule of interest, in particular to the protein of interest;
    detecting a fluorescence resulting from the binding of the HBR analog to the PYP functional derivative, or a functional fragment thereof, and a fluorescence resulting from the binding of the membrane-permeant fluorogenic chromophore to the biological molecule of interest, in particular to the protein of interest;
    measuring the ratio of fluorescence resulting from the binding of the HBR analog to the PYP functional derivative, or a functional fragment thereof, to the fluorescence resulting from the binding of the membrane-permeant fluorogenic chromophore to the biological molecule of interest, in particular to the protein of interest;
    thereby quantifying the fraction of the biological molecule of interest, in particular of the protein of interest, present at least in part at the extra membranous surface of the compartments, or secreted from the compartments, with reference to the whole population of biological molecule of interest, in particular of protein of interest.

In an embodiment, the 4-hydroxybenzylidene-rhodanine (HBR) analog according to the invention and the membrane-permeant fluorogenic chromophore emit in different wavelengths. In an embodiment, the membrane-permeant fluorogenic chromophore binds to the PYP functional derivative, or a functional fragment thereof, as described above. Examples of such membrane-permeant fluorogenic chromophore include, for example, 4-hydroxybenzylidene rhodanine (HBR) and 4-hydroxy-3-methylbenzylidene rhodanine (HMBR).

According to an embodiment, said method of the invention is for quantifying, in a sample comprising cells, the fraction of a biological molecule of interest, in particular a protein of interest, that is present at least in part at the extracellular surface, or secreted from the cells, with reference to the whole population of biological molecule of interest, in particular of protein of interest.

The present invention also relates to an assay relying on the detection of a reporter protein in a sample comprising compartments enclosed by at least one membrane, said assay comprising the steps of:
- obtaining a tagged reporter protein, wherein the reporter protein is tagged with a photoactive yellow protein (PYP) functional derivative, or a functional fragment thereof, as described above;
- contacting the sample with a 4-hydroxybenzylidene-rhodanine (HBR) analog according to the invention; and
- detecting a fluorescence resulting from the binding of the HBR analog to the PYP functional derivative, or a functional fragment thereof;
- thereby detecting the reporter protein present at least in part at the extra membranous surface of the compartments, or secreted from the compartments, through the binding of the HBR analog to the PYP functional derivative, or a functional fragment thereof.

According to an embodiment, said assay relies on the detection of a reporter protein in a sample comprising cells, and allows the detection of the reporter protein present at least in part at the extracellular surface, or secreted from the cells.

According to an embodiment, the assay of the invention is for assessing the activity of a protein of interest involved in the expression or the anchoring of a reporter protein at the membrane or in the secretion of a reporter protein, said method comprising:
- expressing a tagged reporter protein in a sample comprising compartments enclosed by at least one membrane, wherein the protein is tagged with a photoactive yellow protein (PYP) functional derivative, or a functional fragment thereof, as described above and wherein the reporter protein is anchored at the compartment membrane, or secreted as a result of the activity of the protein of interest;
- contacting the sample with a 4-hydroxybenzylidene-rhodanine (HBR) analog according to the invention; and
- detecting a fluorescence resulting from the binding of the HBR analog to the PYP functional derivative, or a functional fragment thereof;
- thereby indirectly assessing the activity of the protein of interest through the binding of the HBR analog to the PYP functional derivative, or a functional fragment thereof.

According to an embodiment, the assay of the invention is a screening method for identifying proteins that are secreted from a compartment enclosed by at least one membrane or localized at the membrane of said compartment using fluorescence as readout.

According to an embodiment, the assay of the invention is a method for detecting interactions between membrane proteins or between a membrane protein and an extracellular protein or a secreted protein using fluorescence as readout.

According to an embodiment, the assay of the invention is a method for detecting protein internalization in a compartment enclosed by at least one membrane or for detecting protein secretion from a compartment enclosed by at least one membrane using fluorescence as readout.

According to an embodiment, the assay of the invention is a FRET assay. In an embodiment, the photoactive yellow protein (PYP) functional derivative, or a functional fragment thereof, as described above plays the acceptor in a pair with a donor such as, for example, CFP. In another embodiment, the photoactive yellow protein (PYP) functional derivative, or a functional fragment thereof, as described above plays the donor in a pair with an acceptor, such as, for example, mCherry.

The present invention also relates to a method for detecting protein trafficking or protein expression at the membrane in a sample comprising compartments enclosed by at least one membrane, wherein said protein trafficking or protein expression at the membrane consists in the localization (e.g. anchoring) of proteins at the membrane of the compartments or in the secretion of proteins from the compartments, said method comprising the steps of:
- expressing a tagged reporter protein in cells, wherein the reporter protein is tagged with a photoactive yellow protein (PYP) functional derivative, or a functional fragment thereof, as described above and wherein the reporter protein is anchored at the membrane or secreted;
- contacting the cells with a 4-hydroxybenzylidene-rhodanine (HBR) analog according to the invention; and
- detecting a fluorescence resulting from the binding of the HBR analog to the PYP functional derivative, or a functional fragment thereof;
- thereby detecting the protein trafficking or protein expression at the membrane through the binding of the HBR analog to the PYP functional derivative, or a functional fragment thereof.

The present invention also relates to a screening method for reporting restoration of protein trafficking or protein expression at the membrane in a sample comprising compartments enclosed by at least one membrane, wherein said protein trafficking or protein expression at the membrane consists in the localization (e.g. anchoring) of proteins at the membrane of the compartments or in the secretion of proteins from the compartments, said method comprising the steps of:
- expressing a tagged reporter protein in cells, wherein the protein is tagged with a photoactive yellow protein (PYP) functional derivative, or a functional fragment thereof, as described above and wherein the reporter protein is anchored at the membrane or secreted;
- incubating the sample with a molecule tested for its ability to restore protein trafficking or protein expression at the membrane;
- contacting the sample with a 4-hydroxybenzylidene-rhodanine (HBR) analog according to the invention; and
- detecting a fluorescence resulting from the binding of the HBR analog to the PYP functional derivative, or a functional fragment thereof;
- thereby detecting the restoration of protein trafficking or protein expression at the membrane through the binding of the HBR analog to the PYP functional derivative, or a functional fragment thereof.

According to an embodiment, said method does not require imaging of the cells. According to an embodiment, the fluorescence is detected by spectrofluorimetry, fluorescence correlation spectroscopy, or flow cytometry.

The present invention also relates to a screening method for reporting inhibition of protein trafficking or protein expression at the membrane in a sample comprising compartments enclosed by at least one membrane, wherein said protein trafficking or protein expression at the membrane consists in the localization (e.g. anchoring) of proteins at the membrane of the compartments or in the secretion of proteins from the compartments, comprising the steps of:
- expressing a tagged reporter protein in cells, wherein the protein is tagged with a photoactive yellow protein (PYP) functional derivative, or a functional fragment thereof, as described above and wherein the reporter protein is anchored at the membrane or secreted;

contacting the sample with a 4-hydroxybenzylidene-rhodanine (HBR) analog according to the invention;

incubating the sample with a molecule tested for its ability to inhibit protein trafficking or protein expression at the membrane;

assessing a lack or decrease of fluorescence resulting from the inability for the HBR analog to bind the PYP functional derivative, or a functional fragment thereof;

thereby detecting the inhibition of protein trafficking or protein expression at the membrane through the lack of binding of the HBR analog to the PYP functional derivative, or a functional fragment thereof.

According to an embodiment, said method does not require imaging of the cells. According to an embodiment, the fluorescence is detected by spectrofluorimetry, fluorescence correlation spectroscopy, or flow cytometry.

EXAMPLES

The present invention is further illustrated by the following examples.

Example 1: HBR Analogs and Manufacture Thereof

Hereafter are presented in Table 1 membrane-impermeant HBR analogs according to the invention.

TABLE 1

| Formula | Reference # Chemical name |
|---|---|
| [structure] | HBRAA # (Z)-2-(5-(4-hydroxybenzylidene)-4-oxo-2-thioxothiazolidin-3-yl)acetic acid |
| [structure] | HBRAA-3M # (Z)-2-(5-(4-hydroxy-3-methylbenzylidene)-4-oxo-2-thioxothiazolidin-3-yl)acetic acid |
| [structure] | HBRAA-3E # (Z)-2-(5-(3-ethyl-4-hydroxybenzylidene)-4-oxo-2-thioxothiazolidin-3-yl)acetic acid |
| [structure] | HBRAA-3OM # (Z)-2-(5-(4-hydroxy-3-methoxybenzylidene)-4-oxo-2-thioxothiazolidin-3-yl)acetic acid |
| [structure] | HBRAA-2OM # (Z)-2-(5-(4-hydroxy-2-methoxybenzylidene)-4-oxo-2-thioxothiazolidin-3-yl)acetic acid |
| [structure] | HBRAA-3OE # (Z)-2-(5-(4-hydroxy-3-ethoxybenzylidene)-4-oxo-2-thioxothiazolidin-3-yl)acetic acid |

TABLE 1-continued

| Formula | Reference # Chemical name |
|---|---|
| 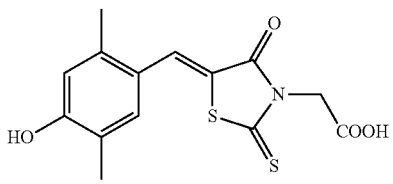 [SMILES: Cc1cc(/C=C2\SC(=S)N(CC(=O)O)C2=O)c(C)cc1O] | HBRAA-2,5DM # (Z)-2-(5-(4-hydroxy-2,5-dimethylbenzylidene)-4-oxo-2-thioxothiazolidin-3-yl)acetic acid |
| 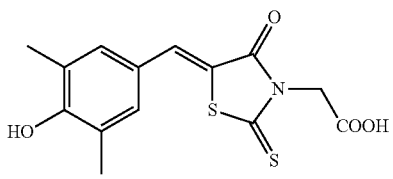 [SMILES: Cc1cc(/C=C2\SC(=S)N(CC(=O)O)C2=O)cc(C)c1O] | HBRAA-3,5DM # (Z)-2-(5-(4-hydroxy-3,5-dimethylbenzylidene)-4-oxo-2-thioxothiazolidin-3-yl)acetic acid |
| 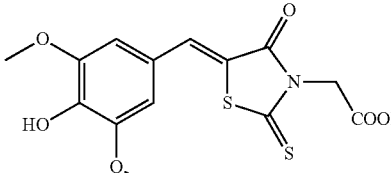 | HBRAA-3,5DOM # (Z)-2-(5-(4-hydroxy-3,5-dimethoxybenzylidene)-4-oxo-2-thioxothiazolidin-3-yl)acetic acid |

The synthesis of these compounds is presented hereafter.

Material and Methods

Commercially available reagents were used as starting materials without further purification.

NMR spectra were recorded on a AC Bruker spectrometer at 300 MHz for $^1$H and 75 MHz for $^{13}$C; chemical shifts are reported in ppm with protonated solvent as internal reference $^1$H, CHCl$_3$ in CDCl$_3$ 7.26 ppm, CHD$_2$SOCD$_3$ in CD$_3$SOCD$_3$ 2.50 ppm; $^{13}$C, $^{13}$CDCl$_3$ in CDCl$_3$ 77.0 ppm, $^{13}$CD$_3$SOCD$_3$ in CD$_3$SOCD$_3$ 39.52 ppm; coupling constants J are given in Hz. Mass spectra were performed by chemical ionization or high resolution. Column chromatography was performed on silica gel 60 (0.040-0.063 nm) Merck. Analytical thin-layer chromatography (TLC) was conducted on Merck silica gel 60 F254 precoated plates.

Results

Synthesis of 4-hydroxy-3-ethylbenzaldehyde

To a solution of 2-ethylphenol (6.1 g, 50 mmol) in 10% aqueous sodium hydroxide (80 mL, 200 mmol) was added trichloromethane (15.0 g, 125 mmol) dropwise at 60° C. over 1 h, and then the reaction mixture was stirred for 2 h at 60° C. After cooling, the mixture was neutralized by an aqueous solution of hydrochloric acid and extracted with dichloromethane. The combined organic layers were washed with brine, dried over magnesium sulfate, and concentrated under reduced pressure. The residue was purified by flash chromatography on silica gel with cyclohexane/ethylacetate (7.5/2.5, v/v) to yield the desired 4-hydroxy-3-ethylbenzaldehyde (1.1 g, 15% yield) as a gray pink solid. $^1$H NMR (300 MHz, CDCl$_3$, δ in ppm): 9.84 (s, 1H), 7.72 (s, 1H), 7.65 (d, J=8.1 Hz, 1H), 6.92 (d, J=8.1 Hz, 1H), 6.51 (s, 1H), 2.70 (q, J=7.5 Hz, 2H), 1.27 (t, J=7.5 Hz, 3H); $^{13}$C NMR (75 MHz, CDCl$_3$, δ in ppm): 192.3, 160.5, 131.5, 131.4, 130.6, 129.4, 115.6, 22.8, 13.5; MS (ESI): m/z 149.2[M–H]$^-$, calcd mass for [C$_9$H$_9$O$_2$]$^-$: 149.1; HRMS (ESI): m/z 149.0608 [M–H]$^-$, calcd mass for [C$_9$H$_9$O$_2$]$^-$: 149.0603.

General Protocol for the Synthesis of HBR Analogs:

A solution containing rhodamine-3-acetic acid (191 mg, 1.0 mmol) and the appropriate substituted 4-hydroxy-benzaldehyde (1.0 mmol) in 40 mL of water was stirred at 90° C. for 7 days. After cooling to 4° C. and standing overnight, the precipitate was filtered through a glass filter and the crude solid was washed with water, ethanol and dried over P$_2$O$_5$, to give the desired product.

(Z)-2-(5-(4-hydroxybenzylidene)-4-oxo-2-thioxothiazolidin-3-yl)acetic Acid (HBRAA)

Yellow powder (41%). $^1$H-NMR (300 MHz, DMSO-d6, δ in ppm). 10.57 (s, 1H), 7.83 (s, 1H), 7.58 (d, J=8.7 Hz, 2H), 6.97 (d, J=8.7 Hz, 2H), 4.75 (s, 2H).

(Z)-2-(5-(4-hydroxy-3-methylbenzylidene)-4-oxo-2-thioxothiazolidin-3-yl)acetic Acid (HBRAA-3M)

Yellow powder (80%). $^1$H NMR (300 MHz, CD$_3$SOCD$_3$, δ in ppm): 10.50 (s, 1H), 7.74 (s, 1H), 7.40 (s, 1H), 7.38 (d, J=8.1 Hz, 1H), 6.96 (d, J=8.1 Hz, 1H), 4.72 (s, 2H), 2.18 (s, 3H); $^{13}$C NMR (75 MHz, CD$_3$SOCD$_3$, δ in ppm): 193.2, 167.4, 166.5, 159.3, 134.9, 134.1, 131.1, 125.7, 123.8, 116.8, 115.8, 45.0, 15.9; MS (ESI): m/z 308.2[M–H]$^-$, calcd mass for [C$_{13}$H$_{10}$NO$_4$S$_2$]$^-$: 308.0; HRMS (ESI): m/z 310.0202 [M+H]$^+$, calcd mass for [C$_{13}$H$_{12}$NO$_4$S$_2$]$^+$: 310.0208.

(Z)-2-(5-(4-hydroxy-2-methoxybenzylidene)-4-oxo-2-thioxothiazolidin-3-yl)acetic Acid (HBRAA-2OM)

Orange powder (74%). $^1$H NMR (300 MHz, CD$_3$SOCD$_3$, δ in ppm): 13.40 (s, 1H), 10.72 (s, 1H), 7.92 (s, 1H), 7.33 (d, J=8.7 Hz, 1H), 6.57 (dd, J=8.4, 2.1 Hz, 1H), 6.53 (d, J=2.1 Hz, 1H), 4.71 (s, 2H), 3.87 (s, 3H); $^{13}$C NMR (75 MHz, CD$_3$SOCD$_3$, δ in ppm): 193.6, 167.4, 166.7, 163.4, 160.6, 132.6, 129.9, 116.6, 112.8, 109.2, 99.4, 55.7, 45.0; MS (ESI): m/z 324.2[M–H]⁻, calcd mass for [C₁₃H₁₀NO₅S₂]⁻: 324.0; HRMS (ESI): m/z 324.0007 [M–H]⁻, calcd mass for [C₁₃H₁₀NO₅S₂]⁻: 324.0000.

(Z)-2-(5-(4-hydroxy-2, 5-dimethylbenzylidene)-4-oxo-2-thioxothiazolidin-3-yl) acetic Acid (HBRAA-2,5DM)

Orange powder (59%). ¹H NMR (300 MHz, CD₃SOCD₃, δ in ppm): 13.43 (s, 1H), 10.36 (s, 1H), 7.86 (s, 1H), 7.17 (s, 1H), 6.77 (s, 1H), 4.72 (s, 2H), 2.36 (s, 3H), 2.15 (s, 3H); ¹³C NMR (75 MHz, CD₃SOCD₃, δ in ppm): 193.5, 167.4, 166.4, 159.0, 140.2, 131.8, 130.9, 123.3, 122.4, 117.8, 117.4, 44.9, 19.2, 15.6; MS (ESI): m/z 322.2 [M–H]⁻, calcd mass for [C₁₄H₁₂NO₄S₂]⁻: 322.0; HRMS (ESI): m/z 322.0214 [M–H]⁻, calcd mass for [C₁₄H₁₂NO₄S₂]⁻: 322.0208.

(Z)-2-(5-(4-hydroxy-3-ethylbenzylidene)-4-oxo-2-thioxothiazolidin-3-yl)acetic Acid (HBRAA-3E)

Yellow powder (62%). ¹H NMR (300 MHz, CD₃SOCD₃, δ in ppm): 13.44 (s, 1H), 10.49 (s, 1H), 7.77 (s, 1H), 7.41 (s, 1H), 7.39 (d, J=7.8 Hz, 1H), 6.97 (d, J=7.8 Hz, 1H), 4.72 (s, 2H), 2.59 (q, J=7.2 Hz, 2H), 1.17 (t, J=7.2 Hz, 3H); ¹³C NMR (75 MHz, CD₃SOCD₃, δ in ppm): 193.1, 167.4, 166.5, 158.9, 135.0, 132.5, 131.5, 131.0, 123.9, 116.8, 116.0, 45.0, 22.5, 13.7; MS (ESI): m/z 322.2 [M–H]⁻, calcd mass for [C₁₄H₁₂NO₄S₂]⁻: 322.0; HRMS (ESI): m/z 322.0212 [M–H]⁻, calcd mass for [C₁₄H₁₂NO₄S₂]⁻: 322.0208.

(Z)-2-(5-(4-hydroxy-3-ethoxybenzylidene)-4-oxo-2-thioxothiazolidin-3-yl)acetic Acid (HBRAA-3OE)

Yellow powder (59%). ¹H NMR (300 MHz, CD₃SOCD₃, δ in ppm): 13.43 (s, 1H), 10.13 (s, 1H), 7.79 (s, 1H), 7.20 (s, 1H), 7.16 (d, J=8.4 Hz, 1H), 6.97 (d, J=8.4 Hz, 1H), 4.73 (s, 2H), 4.10 (q, J=6.9 Hz, 2H), 1.37 (t, J=6.9 Hz, 3H); ¹³C NMR (75 MHz, CD₃SOCD₃, δ in ppm): 193.0, 167.3, 166.4, 150.7, 147.3, 135.0, 125.5, 124.3, 117.2, 116.5, 115.7, 64.0, 45.0, 14.6; MS (ESI): m/z 338.3 [M–H]⁻, calcd mass for [C₁₄H₁₂NO₅S₂]⁻: 338.0; HRMS (ESI): m/z 338.0162 [M–H]⁻, calcd mass for [C₁₄H₁₂NO₅S₂]⁻: 338.0157.

(Z)-2-(5-(4-hydroxy-3-methoxybenzylidene)-4-oxo-2-thioxothiazolidin-3-yl)acetic Acid (HBRAA-3OM)

Yellow powder (55%). ¹H NMR (300 MHz, CD₃SOCD₃, δ in ppm): 13.46 (s, 1H), 10.23 (s, 1H), 7.82 (s, 1H), 7.24 (s, 1H), 7.17 (d, J=8.1 Hz, 1H), 6.97 (d, J=8.1 Hz, 1H), 4.73 (s, 2H), 3.85 (s, 3H); ¹³C NMR (75 MHz, CD₃SOCD₃, δ in ppm): 193.1, 167.4, 166.4, 150.5, 148.2, 135.0, 125.5, 124.3, 117.4, 116.5, 114.7, 55.7, 45.0; MS (ESI): m/z 324.2[M–H]⁻, calcd mass for [C₁₃H₁₀NO₅S₂]⁻: 324.0.

(Z)-2-(5-(4-hydroxy-3, 5-dimethylbenzylidene)-4-oxo-2-thioxothiazolidin-3-yl) acetic Acid (HBRAA-3,5DM)

Orange powder (50%). ¹H NMR (300 MHz, CD₃SOCD₃, δ in ppm): 9.40 (s, 1H), 7.70 (s, 1H), 7.27 (s, 2H), 4.72 (s, 2H), 2.23 (s, 6H); ¹³C NMR (75 MHz, CD₃SOCD₃, δ in ppm): 193.6, 167.8, 166.9, 157.7, 135.3, 132.4 (2C), 126.0 (2C), 124.3, 117.4, 45.4, 17.1 (2C); MS (ESI): m/z 322.2 [M–H]⁻, calcd mass for [C₁₄H₁₂NO₄S₂]⁻: 322.0.

(Z)-2-(5-(4-hydroxy-3, 5-dimethoxybenzylidene)-4-oxo-2-thioxothiazolidin-3-yl) acetic Acid (HBRAA-3,5DOM)

Orange powder (59%). ¹H NMR (300 MHz, CD₃SOCD₃, δ in ppm): 9.63 (s, 1H), 7.82 (s, 1H), 6.97 (s, 2H), 4.73 (s, 2H), 3.85 (s, 6H); ¹³C NMR (75 MHz, CD₃SOCD₃, ν in ppm): 193.4, 167.8, 166.8, 148.8 (2C), 140.2, 135.7, 123.6, 118.1, 109.3 (2C), 56.6 (2C), 45.4; MS (ESI): m/z 354.5 [M–H]⁻, calcd mass for [C₁₄H₁₂NO₆S₂]⁻: 354.0.

Example 2: FAST-HBR Analogs Complexes

Materials and Methods

Bacterial Expression and Protein Purification:

FAST is a variant of the photoactive yellow protein (PYP) containing the mutations C69G, Y94W, T95M, F96I, D97P, Y98T, Q99S, M100R, T101G (SEQ ID NO: 3). His-tagged FAST was expressed in Rosetta(DE3)pLysS $E.$ $coli$ (New England Biolabs). Cells were grown at 37° C. in Lysogeny Broth (LB) medium to $OD_{600\ nm}$ 0.6. Expression was induced for 4 h by adding isopropyl β-D-1-thiogalactopyranoside (IPTG) to a final concentration of 1 mM. Cells were harvested by centrifugation (6,000×g for 15 min at 4° C.) and frozen. The cell pellet was resuspended in lysis buffer (phosphate buffer 50 mM, NaCl 150 mM, $MgCl_2$ 2.5 mM, protease inhibitor, DNase, pH 7.4) and sonicated (5 min at 20% of amplitude). The lysate was incubated for 2 h at 4° C. to allow DNA digestion by DNase. Cellular fragments were removed by centrifugation (15,000×g for 1 h at 4° C.). The supernatant was incubated overnight at 4° C. under gentle agitation with Ni-NTA agarose beads in phosphate buffered saline (PBS) (sodium phosphate 50 mM, NaCl 150 mM, pH 7.4) complemented with 10 mM Imidazole. Beads were washed with 20 volumes of PBS containing 20 mM Imidazole, and with 5 volumes of PBS complemented with 40 mM Imidazole. His-tagged proteins were eluted with 5 volumes of PBS complemented with 0.5 M Imidazole, followed by dialysis with PBS.

Physical Chemistry Experiments:

pH measurements were performed on a standard pH meter PHM210 Radiometer Analytical (calibrated with aqueous buffers at pH 4 and 7 or 10) with a Crison 5208 Electrode (Barcelona, Spain). UV/Vis absorption spectra were recorded in 1 cm×1 cm quartz cuvettes (Hellma) on a diode array UV/Vis spectrophotometer (Evolution array, Thermo Scientific). Corrected fluorescence spectra upon one-photon excitation were recorded with a Photon Technology International QuantaMaster QM-1 spectrofluorimeter (PTI, Monmouth Junction, N.J.) equipped with a Peltier cell holder (TLC50, Quantum Northwest, Shoreline, Wash.). The overall emission quantum yields after one-photon excitation ϕ were determined as previously described (Plamont, M.-A. et al., 2016). Affinity constants were determined by spectrofluorometric titration using a Spark 10M plate reader (Tecan) following protocols previously described (Plamont, M.-A. et al., 2016).

Results

Physico-chemical properties of FAST:fluorogen complexes in PBS pH 7.4 are described in Table 2 below: $\lambda_{abs}$, wavelength of maximal absorption; $\lambda_{em}$, wavelength of maximal emission; ε, molar absorption coefficient at $\lambda_{abs}$; ϕ, fluorescence quantum yield; $K_D$ affinity constant. The brightness is equal to ε×ϕ.

TABLE 2

| Complex | $\lambda_{abs}$ nm | $\lambda_{em}$ nm | ε mM$^{-1}$cm$^{-1}$ | ϕ % | Brightness | $K_D$ μM |
|---|---|---|---|---|---|---|
| FAST:HBR | 467 | 527 | 44 | 9 | 4,000 | 0.62 |
| FAST:HMBR | 481 | 540 | 45 | 23 | 10,300 | 0.13 |
| FAST:HBRAA | 488 | 555 | n.d. | n.d. | n.d. | >20 |
| FAST:HBRAA-3M | 502 | 557 | 56 | 6 | 3,400 | 6.4 |
| FAST:HBRAA-3E | 505 | 559 | 61 | 8 | 4,900 | 1.3 |
| FAST:HBRAA-3OM | 520 | 572 | n.d. | 2 | n.d. | >20 |
| FAST:HBRAA-2OM | 497 | 537 | 55 | 5 | 2,800 | 0.48 |
| FAST:HBRAA-3OE | 525 | 575 | 62 | 6 | 3,700 | 1.7 |
| FAST:HBRAA-2,5DM | 519 | 566 | 63 | 5 | 3,200 | 5.4 |
| FAST:HBRAA-3,5DM | 522 | 571 | n.d. | 4 | n.d. | >20 |
| FAST:HBRAA-3,5DOM | 532 | 606 | n.d. | 1 | n.d. | >20 |

As shown in Table 1, when a potent FAST fluorogenic chromophore such as HBR or HMBR is substituted on the rhodanine head (in $R_3$ position) by a negative group such as carboxymethyl, then its affinity with FAST decrease dramatically: FAST:HBRAA-3M has a $K_D$ which is 40 times higher than corresponding complex FAST:HMBR; and HBRAA has almost no affinity for FAST ($K_D$>20 μM). Moreover, FAST:HBRAA-3M complex exhibited a threefold lower brightness than FAST:HMBR. The molar absorption coefficient of FAST:HRBAA could not even be determined due to low affinity.

Loss of affinity renders the compound unsuitable as fluorogenic chromophore for FAST, whereas moderated brightness is generally considered as disadvantageous when conducted fluoroscopy experiments. Without wishing to be bound by any theory, the Applicant believes that the loss of affinity and brightness results might result from steric clashes between the added carboxymethyl group and FAST.

The Applicant conducted in-depth research in order to solve this issue by engineering the fluorogen structure. By doing so, it was evidenced that the substituents on the aromatic ring are key determinants for the affinity and brightness of FAST:fluorogen complexes. It was also surprisingly found that specific substitutions on the aromatic cycle can restore the affinity between FAST and its fluorogenic chromophore, while others substitutions worsen the stability of the complex.

The properties of complexes formed with FAST by compounds substituted by various groups in various aromatic positions are shown in Table 2.

Switching the methyl group in position 3 to a methoxy group in position 3 resulted in a compound HBRAA-3OM, which has almost no affinity with FAST (Table 2). Moving the methoxy group in position 3 to a methoxy group in position 2 resulted in a compound HBRAA-2OM that bound FAST very strongly with a high affinity of 0.5 μM. The brightness of the complex is however limited to about 2,800 (Table 2).

An alternative modification was the replacement of the methoxy group in position 3 by an ethoxy group in the same position 3, which resulted in HBRAA-3OE compound. This compound display slightly lower affinity of 1.7 μM but form a complex with higher brightness of about 3,700 (Table 2).

The brightest FAST:fluorogen complex was eventually obtained with HBRAA-3E, in which the methyl group in position 3 was replaced by an ethyl group. HBRAA-3E bound FAST with affinities of about 1.3 μM and has a brightness of about 4,900 (Table 1), making it a very interesting candidate for use as membrane-impermeant fluorogenic chromophore.

On the contrary, none of the complexes formed by di-substituted compounds HBRAA-2,5DM, HBRAA-3,5DM and HBRAA-3,5DMO has an affinity higher than the one of HBRAA-3M (Table 2). They should thus not be relevant for cell imaging through FAST tagging.

Although complexes formed between FAST and the membrane-impermeant fluorogenic chromophores according to the invention are not as bright as FAST:HMBR complex (10,300), their brightness are comparable with the brightness of FAST:HBR complex (4,000) and are thus suitable for cell imaging.

Interestingly, FAST:HBRAA-3E exhibited also a 25 nm red shift in absorption and a 20 nm red shift in emission compared to FAST:HMBR and further replacing the ethyl group (HBRAA-3E) by an ethoxy group (HBRAA-3OE) further red-shifted the absorption and the emission of the FAST complex (Table 2).

In conclusion, it was surprisingly found that substitution by an appropriate alkyl or alkoxy group in position 2 or position 3 of the aromatic ring restores the affinity between FAST and the HBR analogue, so that it can be used as fluorogenic chromophore.

Membrane-impermeant fluorogenic chromophores according to the invention are useful for selective imagining methods, as evidenced hereafter.

Example 3: Use of HBR Analogs as Membrane-Impermeant Fluorogenic Chromophores

Materials and Methods
Molecular Biology:

The plasmid pAG211 for mammalian expression of FAST (fused also to mCherry as additional transfection marker) at the outer plasma membrane was obtained by inserting the sequence coding the protein of interest within the pDisplay plasmid (ThermoFisher) using Sal I and Bgl II restriction sites. The plasmid pAG96 for cytoplasmic expression of FAST fused to mCherry was previously reported (Plamont, M.-A. et al., 2016).

Mammalian Cell Culture:

HeLa cells were cultured in DMEM supplemented with phenol red, Glutamax I, 10% (vol/vol) fetal calf serum (FCS), and 1% penicillin-streptomycin at 37° C. within a 5% $CO_2$ atmosphere. For microscopic imaging, cells were seeded in μDish or μSlide IBIDI (Biovalley) coated with poly-L-lysine. Cells were transiently transfected using Genejuice (Merck) according to the manufacturer's protocol. Before imaging, cells were washed with PBS, and treated with DMEM media (without serum and phenol red) containing the fluorogens at the indicated concentration. Cells were imaged directly without washing.

Fluorescence Analysis:

Confocal micrographs were acquired on a Zeiss LSM 710 Laser Scanning Microscope equipped with a Plan Apochromat 63×/1.4 NA oil immersion objective. ZEN software was used to collect the data. Images were analyzed with Image J. Flow cytometry analyses were performed on an Accuri C6 cytometer (BD Biosciences).

The ability of HBR analogs according to the invention to be used as fluorogenic chromophores for labeling cell-surface exposed FAST-tagged proteins in living cells was evaluated. The general principle is illustrated in FIG. 1, which shows the difference in cell labeling between membrane-permeant fluorogens (MPF, FIG. 1a) and membrane-impermeant fluorogens (MIF, FIG. 1b): only cell-surface proteins with at least a part extruding on the extracellular side or secreted proteins are labeled by MIF because they are membrane-impermeant, so that the only marked part of the cell is its membrane. On the contrary, MPF label both internal and external proteins, and thus do not permit selective labeling of cell-surface proteins.

Figure 2:
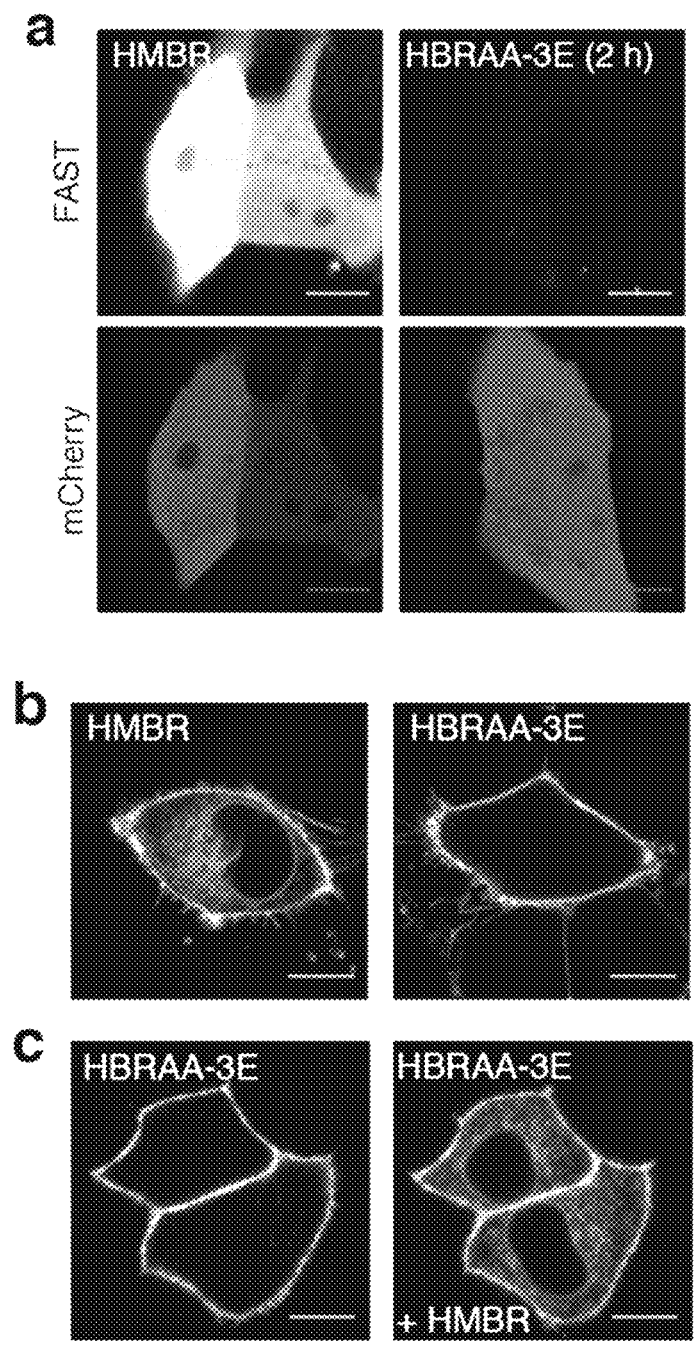
FIG. 2 is a series of photographs showing how membrane-impermeant fluorogens according to the invention can selectively label cell-surface exposed proteins in living cells (scale bars 10 µm). Side-by-side images were recorded using the same settings for direct comparison of the fluorescence intensities. (a) is a series of photographs showing confocal micrographs of HeLa cells expressing FAST fused to the red fluorescent protein mCherry treated with 5µM of membrane-permeant fluorogen of the art (HMBR) for 15 seconds or 5µM of membrane-impermeant fluorogen according to the invention (HBRAA-3E) for 2 hours. (b)-(c) is a series of photographs showing confocal micrographs of HeLa cells expressing FAST fused concomitantly at the N-terminus of the murine Ig K-chain leader sequence and at the C-terminus of the platelet derived growth factor receptor (PDGFR) transmembrane domain displaying FAST on the extracellular side. (b)is a series of photographs showing cells imaged after 5 minutes of treatment with 5 µM membrane-permeant HMBR or membrane-impermeant HBRAA-3E. While HMBR revealed membrane and intracellular proteins, HBRAA-3E revealed only surface-exposed proteins. (c) is a series of photographs showing cells imaged after 1 h of treatment with 5 µM membrane-impermeant HBRAA-3E. Subsequent addition of membrane-permeant HMBR and immediate imaging (<10 s) revealed proteins within the secretory pathway.

Cell exclusion after prolonged exposure was then evaluated. FAST fused to the red fluorescent protein mCherry was expressed in the cytoplasm of HeLa cells. Cells were treated for two hours with media containing 5 µM HBRAA-3E. Confocal imaging revealed no intracellular labeling (FIG. 2a). HBRAA-3E is thus membrane-impermeant and is also a suitable fluorogenic chromophore for long-term studies.

Next, the use of HBRAA-3E for the selective labeling of cell-surface FAST-tagged proteins was studied. A polypeptide was engineered comprising a FAST in between a murine Ig κ-chain leader sequence and the platelet derived growth factor receptor (PDGFR) transmembrane domain. FAST was fused at the N terminus of the murine Ig κ-chain leader sequence, which directs the protein to the secretory pathway and at the C terminus of the PDGFR transmembrane domain, which anchors the protein to the plasma membrane.

The resulting FAST-tagged protein was expressed transiently in HeLa cells. The transfected cells thus displayed FAST on the extracellular side of their membrane. Transfected cells were treated with media containing 5 µM of HMBR or HBRAA-3E for 5 min. While cells treated with membrane permeant HMBR showed labeling of FAST-tagged proteins both at the membrane and within the secretory pathway, cells treated with membrane-impermeant HBRAA-3E showed fluorescent labeling only at the plasma membrane (FIG. 2b).

In addition, no intracellular labeling by HBRAA-3E was observed when longer incubation time (1 h) was used (FIG. 2c), confirming cell exclusion even upon long exposure.

The discovery of small molecules able to restore trafficking defects induced by genetic mutations has become highly important in drug design. Validating the ability of a small molecule to restore normal traffic requires spatial information provided in general by microscopy and image analysis, thus limiting screening throughput. As membrane-impermeant fluorogens such as HBRAA-3E do not label proteins moving within the secretory pathways, they may be used to report on trafficking restoration without the need for imaging.

Conversely, the same set-up may be used to screen for molecules able to prevent normal transport to the cell surface or secretion of chosen proteins. This may allow to block the activity of proteins involved in the development of diseases (such as, for example, virus receptor, signaling molecules, receptor, matrix proteases).

In conclusion, membrane-impermeant fluorogens that bind FAST and give bright fluorescent complex were developed. Their inability to cross the plasma membrane enables to selectively image surface exposed FAST-tagged proteins such as cell-surface proteins, without labeling intracellular proteins. Such staining can be achieved in real-time, without washing, in a single labeling step.

The invention claimed is:

1. A complex formed by a compound of formula (III):

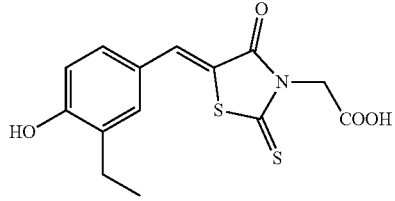

Formula (III)

or a salt thereof;
with a photoactive yellow protein (PYP) functional derivative, or a functional fragment thereof.

2. The complex according to claim 1, wherein the photoactive yellow protein (PYP) functional derivative, or a functional fragment thereof, binds the compound of formula (III) with a $K_D$ lower than about 15 μM when measured at a temperature of about 25° C.

3. A method for detecting a tagged biological molecule of interest in a sample comprising compartments enclosed by at least one membrane, comprising the steps of:
fusing a photoactive yellow protein (PYP) functional derivative, or a functional fragment thereof, to a biological molecule of interest, thereby tagging the biological molecule of interest with the photoactive yellow protein (PYP) functional derivative, or a functional fragment thereof to provide the tagged biological molecule of interest; contacting the sample with a membrane-impermeant fluorogenic chromophore of formula (III):

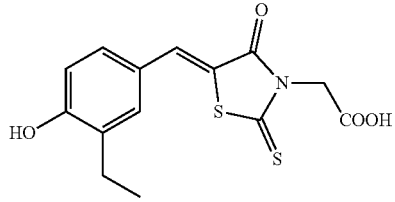

Formula (III)

or a salt thereof; and
detecting a fluorescence resulting from the binding of the membrane-impermeant fluorogenic chromophore of formula (III) to the photoactive yellow protein (PYP) functional derivative, or a functional fragment thereof; thereby detecting the tagged biological molecule of interest present at least in part at the extra membranous surface of the compartments, or secreted from the compartments, through the binding of the membrane-impermeant fluorogenic chromophore of formula (III) to the photoactive yellow protein (PYP) functional derivative, or a functional fragment thereof.

4. The method according to claim 3, wherein the tagged biological molecule of interest is a membrane protein with at least a part of said protein extruding on the outside of said membrane or a secreted protein.

5. The method according to claim 3, wherein the binding of the membrane-impermeant fluorogenic chromophore of formula (III) to the photoactive yellow protein (PYP) functional derivative, or a functional fragment thereof, is reversible.

6. The method according to claim 3, further comprising a step of quantifying the tagged biological molecule of interest by measuring the fluorescence emitted upon binding of the membrane-impermeant fluorogenic chromophore of formula (III) to the photoactive yellow protein (PYP) functional derivative, or a functional fragment thereof, tagged to the biological molecule of interest.

7. The method according to claim 3, wherein the tagged biological molecule of interest is a protein of interest and wherein the method is for sequentially labeling said protein of interest, said method comprising:
fusing the photoactive yellow protein (PYP) functional derivative, or a functional fragment thereof, to the protein of interest, thereby tagging the protein of interest with the PYP functional derivative, or a functional fragment thereof, to provide the tagged protein of interest;
contacting the sample comprising the tagged protein of interest with the membrane-impermeant fluorogenic chromophore of formula (III);
detecting a fluorescence resulting from the binding of the membrane-impermeant fluorogenic chromophore of formula (III) to the PYP functional derivative, or a functional fragment thereof, thereby detecting the fraction of the tagged protein of interest present at least in part at the extra membranous surface of the compartment, or secreted from said compartment;
contacting the sample comprising the tagged protein of interest with a membrane-permeant fluorogenic chromophore able to specifically bind to the tagged protein of interest; detecting a fluorescence resulting from the binding of the membrane-permeant fluorogenic chromophore to the tagged protein of interest, thereby detecting the whole population of the tagged protein of interest.

8. The method according to claim 3, wherein the biological molecule of interest is a reporter protein and wherein the method is for assessing the activity of another protein of interest involved in the expression or the anchoring of the reporter protein at the membrane or in the secretion of the reporter protein through the detection of the reporter protein in the sample comprising compartments enclosed by at least one membrane.
9. A compound of formula (III):
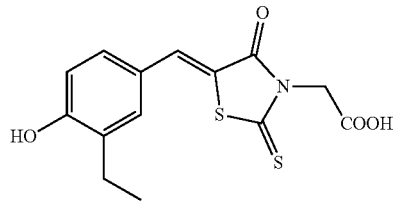
Formula (III)
or a salt thereof.
* * * * *

SEQUENCE LISTING

```
<160> NUMBER OF SEQ ID NOS: 129

<210> SEQ ID NO 1
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      1

<400> SEQUENCE: 1

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ile Ile
                85                  90                  95

Pro Thr Arg Asp Met Pro Thr Lys Val Lys Val His Met Lys Lys Ala
            100                 105                 110
```

```
Leu Ser Gly Asp Ser Tyr Trp Val Phe Val Lys Arg Val
        115                 120                 125

<210> SEQ ID NO 2
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      2

<400> SEQUENCE: 2

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Ile
                85                  90                  95

Pro Thr Leu Pro Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      3

<400> SEQUENCE: 3

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 4
<211> LENGTH: 125
<212> TYPE: PRT
<213> ORGANISM: Artificial Sequence
```

-continued

```
<220> FEATURE:
<223> OTHER INFORMATION: Functional derivative of SEQ ID NO: 48 - Clone
      4

<400> SEQUENCE: 4

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Asp Ile
                85                  90                  95

Pro Thr Asn Pro Glu Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 5
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      5

<400> SEQUENCE: 5

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Thr Glu Cys Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 6
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      6

<400> SEQUENCE: 6

Met Glu His Val Ala Phe Gly Ser Glu Asp Ile Glu Asn Thr Leu Ala
1               5                   10                  15
```

```
Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Ile
                85                  90                  95

Pro Thr Arg Asn Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 7
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      7

<400> SEQUENCE: 7

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Ala Arg Ser Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 8
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      8

<400> SEQUENCE: 8

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60
```

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
            85                  90                  95

Pro Thr Gln Thr Ser Pro Thr Lys Val Lys Val His Met Lys Lys Ala
        100                 105                 110

Leu Ser Gly Asp Ser Tyr Trp Val Phe Val Lys Arg Val
        115                 120                 125

<210> SEQ ID NO 9
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      9

<400> SEQUENCE: 9

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
            85                  90                  95

Pro Thr Glu His Val Pro Thr Lys Val Lys Val His Met Lys Lys Ala
        100                 105                 110

Leu Ser Gly Asp Ser Tyr Trp Val Phe Val Lys Arg Val
        115                 120                 125

<210> SEQ ID NO 10
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      10

<400> SEQUENCE: 10

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ala Ile
            85                  90                  95

Pro Thr His Thr Gln Pro Thr Lys Val Lys Val His Met Lys Lys Ala
        100                 105                 110

Leu Ser Gly Asp Ser Tyr Trp Val Phe Val Lys Arg Val
        115                 120                 125

<210> SEQ ID NO 11
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      11

<400> SEQUENCE: 11

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Ala Gly Lys Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 12
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      12

<400> SEQUENCE: 12

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Ile
                85                  90                  95

Pro Arg Glu Asp Asn Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 13
<211> LENGTH: 125
<212> TYPE: PRT
<213> ORGANISM: Artificial Sequence
<220> FEATURE:

<223> OTHER INFORMATION: Functional derivative of SEQ ID NO: 48 - Clone
      13

<400> SEQUENCE: 13

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Gln Ile Met Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      14

<400> SEQUENCE: 14

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Val
                85                  90                  95

Pro Arg Ile Cys Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 15
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      15

<400> SEQUENCE: 15

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln

```
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Thr Ile
                    85                  90                  95

Pro Ala Leu Arg Lys Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 16
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      16

<400> SEQUENCE: 16

Met Glu His Val Ala Phe Gly Ser Glu Asp Ile Glu Asn Thr Leu Ala
  1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp His Ile
                    85                  90                  95

Pro Arg Asp Pro His Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 17
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      17

<400> SEQUENCE: 17

Met Glu His Val Ala Phe Gly Ser Glu Asp Ile Glu Asn Thr Leu Ala
  1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
```

```
            65                  70                  75                  80
Glu Gly Val Ala Ser Gly Asn Leu Asn Thr Met Phe Glu Trp Ser Ile
                    85                  90                  95

Pro Val Ser Gly Gln Pro Thr Lys Val Lys Val His Met Lys Lys Ala
                100                 105                 110

Leu Ser Gly Asp Ser Tyr Trp Val Phe Val Lys Arg Val
                115                 120                 125

<210> SEQ ID NO 18
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      18

<400> SEQUENCE: 18

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
                35                  40                  45

Ile Thr Gly Arg Asp Pro Lys Gln Val Ile Gly Lys Asn Phe Phe Lys
            50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Val
                    85                  90                  95

Pro Thr Phe Ile Val Pro Thr Lys Val Lys Val His Met Lys Lys Ala
                100                 105                 110

Leu Ser Gly Asp Ser Tyr Trp Val Phe Val Lys Arg Val
                115                 120                 125

<210> SEQ ID NO 19
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      19

<400> SEQUENCE: 19

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
                35                  40                  45

Ile Thr Gly Arg Asp Pro Lys Gln Val Ile Gly Lys Asn Phe Phe Lys
            50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
                    85                  90                  95

Pro Ala Asn His Lys Pro Thr Lys Val Lys Val His Met Lys Lys Ala
                100                 105                 110

Leu Ser Gly Asp Ser Tyr Trp Val Phe Val Lys Arg Val
```

-continued

```
<210> SEQ ID NO 20
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      20

<400> SEQUENCE: 20

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Ile
                85                  90                  95

Pro Pro Phe Glu Ser Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 21
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      21

<400> SEQUENCE: 21

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Val
                85                  90                  95

Pro Asn Pro Ile Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 22
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
```

22

<400> SEQUENCE: 22

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Gln Ile
                85                  90                  95

Pro Val Tyr Ala Val Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 23
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      23

<400> SEQUENCE: 23

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Gln Ile
                85                  90                  95

Pro Thr Ser Ile Ile Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 24
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      24

<400> SEQUENCE: 24

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

```
Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Met Ile
                85                  90                  95

Pro Gly Asp Gly Asp Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 25
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      25

<400> SEQUENCE: 25

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Asp Ile
                85                  90                  95

Pro His Asp Asp Ala Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      26

<400> SEQUENCE: 26

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
 65                  70                  75                  80
```

```
Glu Gly Val Ala Ser Gly Asn Leu Asn Thr Met Phe Glu Trp Ser Ile
                85                  90                  95

Pro Ser Val Arg His Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      27

<400> SEQUENCE: 27

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Phe Ile
                85                  90                  95

Pro Lys Gly His Lys Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 28
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      28

<400> SEQUENCE: 28

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Lys Pro Thr Ala Pro Thr Lys Val Lys Val His Met Lys Lys Ala
            100                 105                 110

Leu Ser Gly Asp Ser Tyr Trp Val Phe Val Lys Arg Val
        115                 120                 125
```

<210> SEQ ID NO 29
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 29

<400> SEQUENCE: 29

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ala Val
                85                  90                  95

Pro Gly Val Cys Gly Pro Thr Lys Val Lys Val His Met Lys Lys Ala
            100                 105                 110

Leu Ser Gly Asp Ser Tyr Trp Val Phe Val Lys Arg Val
        115                 120                 125
```

<210> SEQ ID NO 30
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 30

<400> SEQUENCE: 30

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Gly Glu Met Phe Pro Thr Lys Val Lys Val His Met Lys Lys Ala
            100                 105                 110

Leu Ser Gly Asp Ser Tyr Trp Val Phe Val Lys Arg Val
        115                 120                 125
```

<210> SEQ ID NO 31
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 31

<400> SEQUENCE: 31

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Val
                85                  90                  95

Pro Thr Thr Arg Leu Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 32
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 32

<400> SEQUENCE: 32

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Phe Val
                85                  90                  95

Pro Gly Pro Ser Val Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 33
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 33

<400> SEQUENCE: 33

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30
```

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Arg Arg Val Val Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 34
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      34

<400> SEQUENCE: 34

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Leu
                85                  90                  95

Pro Ala Trp His His Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 35
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      35

<400> SEQUENCE: 35

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                  70                  75                  80

```
Glu Gly Val Ala Ser Gly Asn Leu Asn Thr Met Phe Glu Trp Thr Ile
            85                  90                  95
Pro Val Leu Gly Thr Pro Thr Lys Val Lys Val His Met Lys Lys Ala
            100                 105                 110
Leu Ser Gly Asp Ser Tyr Trp Val Phe Val Lys Arg Val
            115                 120             125

<210> SEQ ID NO 36
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      36

<400> SEQUENCE: 36

Met Glu His Val Ala Phe Gly Ser Glu Asp Ile Glu Asn Thr Leu Ala
1               5                   10                  15
Lys Met Asp Asp Gly Gln Leu Asp Gly Leu Ala Phe Gly Ala Ile Gln
            20                  25                  30
Leu Asp Gly Asp Gly Asn Ile Leu Gln Tyr Asn Ala Ala Glu Gly Asp
            35                  40                  45
Ile Thr Gly Arg Asp Pro Lys Gln Val Ile Gly Lys Asn Phe Phe Lys
50                  55                  60
Asp Val Ala Pro Gly Thr Asp Ser Pro Glu Phe Tyr Gly Lys Phe Lys
65                  70                  75                  80
Glu Gly Val Ala Ser Gly Asn Leu Asn Thr Met Phe Glu Trp Glu Ile
            85                  90                  95
Pro Ile Pro Thr Asn Pro Thr Lys Val Lys Val His Met Lys Lys Ala
            100                 105                 110
Leu Ser Gly Asp Ser Tyr Trp Val Phe Val Lys Arg Val
            115                 120             125

<210> SEQ ID NO 37
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      37

<400> SEQUENCE: 37

Met Glu His Val Ala Phe Gly Ser Glu Asp Ile Glu Asn Thr Leu Ala
1               5                   10                  15
Lys Met Asp Asp Gly Gln Leu Asp Gly Leu Ala Phe Gly Ala Ile Gln
            20                  25                  30
Leu Asp Gly Asp Gly Asn Ile Leu Gln Tyr Asn Ala Ala Glu Gly Asp
            35                  40                  45
Ile Thr Gly Arg Asp Pro Lys Gln Val Ile Gly Lys Asn Phe Phe Lys
50                  55                  60
Asp Val Ala Pro Gly Thr Asp Ser Pro Glu Phe Tyr Gly Lys Phe Lys
65                  70                  75                  80
Glu Gly Val Ala Ser Gly Asn Leu Asn Thr Met Phe Glu Trp Val Ile
            85                  90                  95
Pro Asn Tyr Thr Met Pro Thr Lys Val Lys Val His Met Lys Lys Ala
            100                 105                 110
Leu Ser Gly Asp Ser Tyr Trp Val Phe Val Lys Arg Val
            115                 120             125
```

<210> SEQ ID NO 38
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 38

<400> SEQUENCE: 38

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
                85                  90                  95

Pro Ala Leu His Trp Pro Thr Lys Val Lys Val His Met Lys Lys Ala
            100                 105                 110

Leu Ser Gly Asp Ser Tyr Trp Val Phe Val Lys Arg Val
        115                 120                 125
```

<210> SEQ ID NO 39
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 39

<400> SEQUENCE: 39

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Gly Ile
                85                  90                  95

Pro Thr Pro Glu Glu Pro Thr Lys Val Lys Val His Met Lys Lys Ala
            100                 105                 110

Leu Ser Gly Asp Ser Tyr Trp Val Phe Val Lys Arg Val
        115                 120                 125
```

<210> SEQ ID NO 40
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 40

```
<400> SEQUENCE: 40

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Glu Ile
                85                  90                  95

Pro Met Gly Ala His Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 41
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      41

<400> SEQUENCE: 41

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Pro Gly Arg Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 42
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      42

<400> SEQUENCE: 42

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
```

```
                35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Asn Leu
                 85                  90                  95

Pro Val Lys Ala Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 43
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      43

<400> SEQUENCE: 43

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
             20                  25                  30

Leu Asp Gly Asp Gly Asn Ile Leu Gln Tyr Asn Ala Ala Glu Gly Asp
             35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Glu Val
                 85                  90                  95

Pro Ala Glu Thr Met Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      44

<400> SEQUENCE: 44

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
             20                  25                  30

Leu Asp Gly Asp Gly Asn Ile Leu Gln Tyr Asn Ala Ala Glu Gly Asp
             35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Arg Val
```

```
                    85                  90                  95

Pro Asn Pro Thr Gly Pro Thr Lys Val Lys Val His Met Lys Lys Ala
                100                 105                 110

Leu Ser Gly Asp Ser Tyr Trp Val Phe Val Lys Arg Val
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      45

<400> SEQUENCE: 45

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Ile
                85                  90                  95

Pro Lys Pro Phe Ile Pro Thr Lys Val Lys Val His Met Lys Lys Ala
                100                 105                 110

Leu Ser Gly Asp Ser Tyr Trp Val Phe Val Lys Arg Val
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      46

<400> SEQUENCE: 46

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Val
                85                  90                  95

Pro Ser Thr Arg Leu Pro Thr Lys Val Lys Val His Met Lys Lys Ala
                100                 105                 110

Leu Ser Gly Asp Ser Tyr Trp Val Phe Val Lys Arg Val
        115                 120                 125
```

```
<210> SEQ ID NO 47
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      47

<400> SEQUENCE: 47
```

| Met | Glu | His | Val | Ala | Phe | Gly | Ser | Glu | Asp | Ile | Glu | Asn | Thr | Leu | Ala |
|---|---|---|---|---|---|---|---|---|---|---|---|---|---|---|---|
| 1 | | | | 5 | | | | | 10 | | | | | 15 | |

| Lys | Met | Asp | Asp | Gly | Gln | Leu | Asp | Gly | Leu | Ala | Phe | Gly | Ala | Ile | Gln |
|---|---|---|---|---|---|---|---|---|---|---|---|---|---|---|---|
| | | | 20 | | | | | 25 | | | | | 30 | | |

| Leu | Asp | Gly | Asp | Gly | Asn | Ile | Leu | Gln | Tyr | Asn | Ala | Ala | Glu | Gly | Asp |
|---|---|---|---|---|---|---|---|---|---|---|---|---|---|---|---|
| | | 35 | | | | | 40 | | | | | 45 | | | |

| Ile | Thr | Gly | Arg | Asp | Pro | Lys | Gln | Val | Ile | Gly | Lys | Asn | Phe | Phe | Lys |
|---|---|---|---|---|---|---|---|---|---|---|---|---|---|---|---|
| | 50 | | | | | 55 | | | | | 60 | | | | |

| Asp | Val | Ala | Pro | Gly | Thr | Asp | Ser | Pro | Glu | Phe | Tyr | Gly | Lys | Phe | Lys |
|---|---|---|---|---|---|---|---|---|---|---|---|---|---|---|---|
| 65 | | | | | 70 | | | | | 75 | | | | | 80 |

| Glu | Gly | Val | Ala | Ser | Gly | Asn | Leu | Asn | Thr | Met | Phe | Glu | Arg | Trp | Ile |
|---|---|---|---|---|---|---|---|---|---|---|---|---|---|---|---|
| | | | | 85 | | | | | 90 | | | | | 95 | |

| Pro | Gly | Lys | Met | Val | Pro | Thr | Lys | Val | Lys | Val | His | Met | Lys | Lys | Ala |
|---|---|---|---|---|---|---|---|---|---|---|---|---|---|---|---|
| | | | 100 | | | | | 105 | | | | | 110 | | |

| Leu | Ser | Gly | Asp | Ser | Tyr | Trp | Val | Phe | Val | Lys | Arg | Val |
|---|---|---|---|---|---|---|---|---|---|---|---|---|
| | | 115 | | | | | 120 | | | | | 125 |

```
<210> SEQ ID NO 48
<211> LENGTH: 125
<212> TYPE: PRT
<213> ORGANISM: Halorhodospira halophila
<220> FEATURE:
<223> OTHER INFORMATION: C69G variant

<400> SEQUENCE: 48
```

| Met | Glu | His | Val | Ala | Phe | Gly | Ser | Glu | Asp | Ile | Glu | Asn | Thr | Leu | Ala |
|---|---|---|---|---|---|---|---|---|---|---|---|---|---|---|---|
| 1 | | | | 5 | | | | | 10 | | | | | 15 | |

| Lys | Met | Asp | Asp | Gly | Gln | Leu | Asp | Gly | Leu | Ala | Phe | Gly | Ala | Ile | Gln |
|---|---|---|---|---|---|---|---|---|---|---|---|---|---|---|---|
| | | | 20 | | | | | 25 | | | | | 30 | | |

| Leu | Asp | Gly | Asp | Gly | Asn | Ile | Leu | Gln | Tyr | Asn | Ala | Ala | Glu | Gly | Asp |
|---|---|---|---|---|---|---|---|---|---|---|---|---|---|---|---|
| | | 35 | | | | | 40 | | | | | 45 | | | |

| Ile | Thr | Gly | Arg | Asp | Pro | Lys | Gln | Val | Ile | Gly | Lys | Asn | Phe | Phe | Lys |
|---|---|---|---|---|---|---|---|---|---|---|---|---|---|---|---|
| | 50 | | | | | 55 | | | | | 60 | | | | |

| Asp | Val | Ala | Pro | Gly | Thr | Asp | Ser | Pro | Glu | Phe | Tyr | Gly | Lys | Phe | Lys |
|---|---|---|---|---|---|---|---|---|---|---|---|---|---|---|---|
| 65 | | | | | 70 | | | | | 75 | | | | | 80 |

| Glu | Gly | Val | Ala | Ser | Gly | Asn | Leu | Asn | Thr | Met | Phe | Glu | Tyr | Thr | Phe |
|---|---|---|---|---|---|---|---|---|---|---|---|---|---|---|---|
| | | | | 85 | | | | | 90 | | | | | 95 | |

| Asp | Tyr | Gln | Met | Thr | Pro | Thr | Lys | Val | Lys | Val | His | Met | Lys | Lys | Ala |
|---|---|---|---|---|---|---|---|---|---|---|---|---|---|---|---|
| | | | 100 | | | | | 105 | | | | | 110 | | |

| Leu | Ser | Gly | Asp | Ser | Tyr | Trp | Val | Phe | Val | Lys | Arg | Val |
|---|---|---|---|---|---|---|---|---|---|---|---|---|
| | | 115 | | | | | 120 | | | | | 125 |

```
<210> SEQ ID NO 49
<211> LENGTH: 125
<212> TYPE: PRT
<213> ORGANISM: Halorhodospira halophila

<400> SEQUENCE: 49
```

| Met | Glu | His | Val | Ala | Phe | Gly | Ser | Glu | Asp | Ile | Glu | Asn | Thr | Leu | Ala |
|---|---|---|---|---|---|---|---|---|---|---|---|---|---|---|---|
| 1 | | | | 5 | | | | | 10 | | | | | 15 | |

```
Lys Met Asp Asp Gly Gln Leu Asp Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Cys Thr Asp Ser Pro Glu Phe Tyr Gly Lys Phe Lys
 65                  70                  75                  80

Glu Gly Val Ala Ser Gly Asn Leu Asn Thr Met Phe Glu Tyr Thr Phe
                85                  90                  95

Asp Tyr Gln Met Thr Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 50
<211> LENGTH: 125
<212> TYPE: PRT
<213> ORGANISM: Halomonas boliviensis LC1

<400> SEQUENCE: 50

```
Met Glu Thr Val Arg Phe Gly Gly Asp Asp Ile Glu Asn Ser Leu Ala
  1               5                  10                  15

Lys Met Asp Asp Lys Lys Leu Asp Glu Leu Ala Phe Gly Ala Ile Gln
            20                  25                  30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
 50                  55                  60

Glu Val Ala Pro Cys Thr Gln Ser Lys Glu Phe Gln Gly Arg Phe Lys
 65                  70                  75                  80

Glu Gly Val Ser Ser Gly Glu Leu Asn Thr Met Phe Glu Tyr Val Phe
                85                  90                  95

Asp Tyr Gln Met Thr Pro Thr Lys Val Lys Val His Met Lys Lys Ala
            100                 105                 110

Ile Ser Gly Asp Thr Tyr Trp Ile Phe Val Lys Arg Leu
            115                 120                 125
```

<210> SEQ ID NO 51
<211> LENGTH: 125
<212> TYPE: PRT
<213> ORGANISM: Halomonas sp. GFAJ-1

<400> SEQUENCE: 51

```
Met Glu Thr Val Arg Phe Gly Gly Asp Asp Ile Glu Asn Ala Leu Ala
  1               5                  10                  15

Asn Met Asp Asp Lys Lys Leu Asp Thr Leu Ala Phe Gly Ala Ile Gln
            20                  25                  30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
 50                  55                  60

Asp Val Ala Pro Cys Thr Gln Ser Lys Glu Phe Gln Gly Arg Phe Lys
 65                  70                  75                  80

Glu Gly Val Lys Asn Gly Asp Leu Asn Thr Met Phe Glu Tyr Val Phe
                85                  90                  95
```

Asp Tyr Gln Met Thr Pro Thr Lys Val Lys Val His Met Lys Lys Ala
              100                 105                 110

Leu Ser Gly Asp Thr Phe Trp Ile Phe Val Lys Arg Leu
        115                 120                 125

<210> SEQ ID NO 52
<211> LENGTH: 125
<212> TYPE: PRT
<213> ORGANISM: Rheinheimera sp. A13L

<400> SEQUENCE: 52

Leu Glu Thr Val Arg Phe Gly Gly Asp Asp Ile Glu Asn Ser Leu Ala
1               5                   10                  15

Lys Met Asp Asp Lys Ala Leu Asp Lys Leu Ala Phe Gly Ala Ile Gln
            20                  25                  30

Leu Asp Gly Asn Gly Lys Ile Ile His Tyr Asn Ala Ala Glu Gly Thr
        35                  40                  45

Ile Thr Gly Arg Asp Pro Lys Thr Val Ile Gly Lys Asn Phe Phe Thr
    50                  55                  60

Asp Val Ala Pro Cys Thr Gln Ser Lys Glu Phe Gln Gly Arg Phe Lys
65                  70                  75                  80

Glu Gly Val Gln Lys Gly Asp Leu Asn Thr Met Phe Glu Tyr Val Phe
                85                  90                  95

Asp Tyr Gln Met Lys Pro Thr Lys Val Lys Val His Met Lys Lys Ala
            100                 105                 110

Met Thr Gly Asp Ser Phe Trp Ile Phe Val Lys Arg Leu
        115                 120                 125

<210> SEQ ID NO 53
<211> LENGTH: 125
<212> TYPE: PRT
<213> ORGANISM: Idiomarina loihiensis

<400> SEQUENCE: 53

Met Glu Ile Val Gln Phe Gly Ser Asp Asp Ile Glu Asn Thr Leu Ser
1               5                   10                  15

Lys Met Ser Asp Lys Leu Asn Asp Ile Ala Phe Gly Ala Ile Gln
            20                  25                  30

Leu Asp Ala Ser Gly Lys Ile Ile Gln Tyr Asn Ala Ala Glu Gly Asp
        35                  40                  45

Ile Thr Gly Arg Asp Pro Gly Ala Val Val Gly Lys Asn Phe Phe Asn
    50                  55                  60

Glu Val Ala Pro Cys Thr Asn Ser Pro Glu Phe Lys Gly Arg Phe Asp
65                  70                  75                  80

Glu Gly Val Lys Asn Gly Asn Leu Asn Thr Met Phe Glu Tyr Val Phe
                85                  90                  95

Asp Tyr Glu Met Gln Pro Thr Lys Val Lys Val His Met Lys Lys Ala
            100                 105                 110

Leu Thr Gly Asp Thr Tyr Trp Val Phe Val Lys Arg Leu
        115                 120                 125

<210> SEQ ID NO 54
<211> LENGTH: 125
<212> TYPE: PRT
<213> ORGANISM: Thiorhodospira sibirica ATCC 700588

<400> SEQUENCE: 54

Met Glu Leu Leu Ser Phe Gly Ala Asp Asn Ile Glu Asn Ser Leu Ala

```
                1               5                  10                  15
Lys Met Ser Lys Gly Asp Leu Asn Lys Leu Ala Phe Gly Ala Ile Gln
                    20                  25                  30

Leu Asn Ala Gln Gly Lys Ile Leu Gln Tyr Asn Ala Ala Glu Gly Asp
                    35                  40                  45

Ile Thr Gly Arg Lys Pro Thr Glu Val Ile Gly Lys Asn Phe Phe Leu
            50                  55                  60

Glu Val Ala Pro Cys Thr Asn Arg Thr Glu Phe Lys Gly Arg Phe Asp
65                  70                  75                  80

Gln Gly Ile Lys Ser Gly Asn Leu Asn Thr Met Phe Glu Tyr Thr Phe
                        85                  90                  95

Asp Tyr Glu Met Lys Pro Thr Lys Val Lys Val His Met Lys Lys Ala
                    100                 105                 110

Leu Val Asp Asp Thr Tyr Trp Val Phe Val Lys Arg Val
                115                 120                 125
```

<210> SEQ ID NO 55
<211> LENGTH: 125
<212> TYPE: PRT
<213> ORGANISM: Rhodothalassium salexigens

<400> SEQUENCE: 55

```
Met Glu Met Ile Lys Phe Gly Gln Asp Asp Ile Glu Asn Ala Met Ala
1               5                   10                  15

Asp Met Gly Asp Ala Gln Ile Asp Leu Ala Phe Gly Ala Ile Gln
                    20                  25                  30

Leu Asp Glu Thr Gly Thr Ile Leu Ala Tyr Asn Ala Ala Glu Gly Glu
                    35                  40                  45

Leu Thr Gly Arg Ser Pro Gln Asp Val Ile Gly Lys Asn Phe Phe Lys
                50                  55                  60

Asp Ile Ala Pro Cys Thr Asp Thr Glu Glu Phe Gly Gly Arg Phe Arg
65                  70                  75                  80

Glu Gly Val Ala Asn Gly Asp Leu Asn Ala Met Phe Glu Tyr Val Phe
                        85                  90                  95

Asp Tyr Gln Met Gln Pro Thr Lys Val Lys Val His Met Lys Arg Ala
                    100                 105                 110

Ile Thr Gly Asp Ser Tyr Trp Ile Phe Val Lys Arg Val
                115                 120                 125
```

<210> SEQ ID NO 56
<211> LENGTH: 124
<212> TYPE: PRT
<213> ORGANISM: Roseomonas cervicalis ATCC 49957

<400> SEQUENCE: 56

```
Met Glu Leu Leu Lys Phe Gly Thr Asp Asp Ile Asp Asn Leu Val Ala
1               5                   10                  15

Arg Asp Pro Ser Arg Leu Asp Arg Leu Pro Phe Gly Ala Val Leu Leu
                    20                  25                  30

Asp Arg Thr Gly Arg Val Thr Lys Tyr Asn Ala Gly Glu Val Ala Ile
                    35                  40                  45

Ser Gly Arg Thr Ala Asp Gln Val Leu Gly Lys Asn Phe Phe Asn Asp
            50                  55                  60

Ile Ala Pro Cys Thr Lys Gly His Gln Phe Met Gly Arg Phe Asn Gln
65                  70                  75                  80

Ala Leu Ala Gln Gly Ser Ile Asn Thr Met Phe Glu Tyr Ala Phe Asp
```

-continued

```
                85                  90                  95
Tyr Lys Met Lys Pro Ala Lys Val Arg Val His Met Lys Ser Val Ser
            100                 105                 110
Ile Asp Gln Gly Ile Trp Val Phe Ile Lys Arg Leu
            115                 120

<210> SEQ ID NO 57
<211> LENGTH: 124
<212> TYPE: PRT
<213> ORGANISM: Rhodobacter sphaeroides

<400> SEQUENCE: 57

Met Glu Ile Ile Pro Phe Gly Ser Ala Asp Leu Asp Asn Ile Leu Ala
1               5                   10                  15

Arg Glu Pro Gln Arg Ala Glu Tyr Leu Pro Phe Gly Ala Val Leu Leu
            20                  25                  30

Asp Arg Thr Gly Thr Ile Leu Lys Tyr Asn Arg Ala Glu Gly Gly Ile
            35                  40                  45

Ala Asn Arg Asn Pro Ala Asp Val Ile Gly Lys Asn Phe Phe Asn Glu
        50                  55                  60

Ile Ala Pro Cys Ala Lys Gly Lys Arg Phe His Gly Glu Phe Leu Arg
65                  70                  75                  80

Phe His Gln Thr Gly Gln Val Asn Val Met Phe Asp Tyr Lys Phe Ala
                85                  90                  95

Tyr Lys Gly Ala Asn Val Gly Val Lys Ile His Met Lys Ser Gln Pro
            100                 105                 110

Asp Gly Gln Ser Cys Trp Leu Phe Val Lys Arg Val
            115                 120

<210> SEQ ID NO 58
<211> LENGTH: 112
<212> TYPE: PRT
<213> ORGANISM: Leptospira wolbachii

<400> SEQUENCE: 58

Ser Asn Lys Leu Gly Thr Leu Thr Gln Ala Glu Ala Asp Ala Ala Ala
1               5                   10                  15

Phe Gly Ile Val Lys Val Asp Gly Asn Gly Lys Ile Leu Leu Tyr Asn
            20                  25                  30

Lys Tyr Glu Ser Glu Leu Ser Asn Leu Pro Asn Asp Thr Val Ile Gly
            35                  40                  45

Lys Asn Phe Phe Thr Glu Val Ala Ile Cys Ala Asn Asn Arg Ile Phe
        50                  55                  60

Tyr Gly Lys Phe Lys Glu Gly Met Val Ser Lys Asn Leu Asp Thr Ala
65                  70                  75                  80

Phe Asn Tyr Val Phe Thr Tyr Arg Met Lys Pro Thr Asn Val Leu Ile
                85                  90                  95

His Leu Tyr Tyr Asp Lys Thr Ser Asp Ser Asn Trp Ile Phe Val Lys
            100                 105                 110

<210> SEQ ID NO 59
<211> LENGTH: 123
<212> TYPE: PRT
<213> ORGANISM: Rhodobacter capsulatus

<400> SEQUENCE: 59

Met Glu Ile Ile Pro Phe Gly Thr Asn Asp Ile Asp Asn Ile Leu Ala
1               5                   10                  15
```

```
Arg Glu Pro Ala Arg Ala Glu Ser Leu Pro Phe Gly Ala Val Leu Leu
            20                  25                  30

Asp Arg Met Gly Arg Ile Ala Lys Tyr Asn Lys Ala Glu Gly Leu Ile
        35                  40                  45

Ala Gly Arg Asp Pro Ser Thr Val Ile Gly Arg Asp Phe Phe Asn Glu
 50                  55                  60

Ile Ala Pro Cys Ala Lys Gly Lys Arg Phe His Gly Glu Phe Leu Lys
 65                  70                  75                  80

Phe Asn Arg Thr Gly Gln Ala Asn Val Met Leu Asp Tyr Lys Phe Asn
                85                  90                  95

Tyr Lys Gly Ala Glu Val Ala Val Lys Ile His Leu Lys Ser Gln Pro
            100                 105                 110

Asp Gly Gln Phe Cys Trp Leu Phe Val Lys Arg
            115                 120

<210> SEQ ID NO 60
<211> LENGTH: 117
<212> TYPE: PRT
<213> ORGANISM: Rhodospirillum centenum

<400> SEQUENCE: 60

Thr Glu Gln Ile Arg Gly Thr Ile Asp Gly Met Gly Thr Ala Glu Phe
1               5                   10                  15

Asp Ala Leu Pro Val Gly Ala Ile Gln Val Asp Gly Ser Gly Val Ile
            20                  25                  30

His Arg Tyr Asn Arg Thr Glu Ser Arg Leu Ser Gly Arg Ile Pro Glu
        35                  40                  45

Arg Val Ile Gly Arg Asn Phe Phe Thr Glu Val Ala Pro Cys Thr Asn
 50                  55                  60

Ile Pro Ala Phe Ser Gly Arg Phe Met Asp Gly Val Thr Ser Gly Thr
 65                  70                  75                  80

Leu Asp Ala Arg Phe Asp Phe Val Phe Asp Gln Met Ala Pro Val
                85                  90                  95

Arg Val Gln Ile Arg Met Gln Asn Ala Gly Val Pro Asp Arg Tyr Trp
            100                 105                 110

Ile Phe Val Arg Lys
            115

<210> SEQ ID NO 61
<211> LENGTH: 112
<212> TYPE: PRT
<213> ORGANISM: Leptospira vanthielii

<400> SEQUENCE: 61

Ser Asn Lys Leu Gly Thr Leu Thr Gln Ala Glu Ala Asp Ala Ala Ala
1               5                   10                  15

Phe Gly Ile Val Lys Val Asp Gly Asn Gly Lys Ile Leu Leu Tyr Asn
            20                  25                  30

Lys Tyr Glu Ser Glu Leu Ser Asn Leu Pro Asn Asp Thr Val Ile Gly
        35                  40                  45

Lys Asn Phe Phe Thr Glu Val Ala Ile Cys Ala Asn Asn Arg Ile Phe
 50                  55                  60

Tyr Gly Lys Phe Lys Glu Gly Met Val Thr Lys Asn Leu Asp Thr Ala
 65                  70                  75                  80

Phe Asn Tyr Val Phe Thr Tyr Arg Met Lys Pro Thr Asn Val Leu Ile
                85                  90                  95
```

His Leu Tyr Tyr Asp Lys Thr Ser Asp Thr Asn Trp Ile Phe Val Lys
            100                 105                 110

<210> SEQ ID NO 62
<211> LENGTH: 118
<212> TYPE: PRT
<213> ORGANISM: Leptospira terpstrae

<400> SEQUENCE: 62

Phe Ile Asp Pro Asn Ile Leu Gly Lys Leu Gly Thr Leu Thr Gln Ala
1               5                   10                  15

Glu Ala Asp Ala Ala Ala Phe Gly Val Val Lys Val Asp Gly Asn Gly
            20                  25                  30

Lys Ile Leu Leu Tyr Asn Lys Tyr Glu Ser Glu Leu Ala Asn Val Pro
        35                  40                  45

Ile Gln Thr Ala Val Gly Lys Asn Phe Phe Thr Glu Val Ala Ile Cys
    50                  55                  60

Thr Asn Asn Arg Ile Phe Tyr Gly Arg Phe Lys Glu Gly Met Leu Thr
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Thr Ser Asp Thr
            100                 105                 110

Asn Trp Ile Phe Val Lys
            115

<210> SEQ ID NO 63
<211> LENGTH: 118
<212> TYPE: PRT
<213> ORGANISM: Leptospira biflexa serovar Patoc strain 'Patoc 1
    (Paris)'

<400> SEQUENCE: 63

Phe Ile Asp Pro Asn Ile Leu Gly Lys Leu Gly Thr Leu Ala Gln Ala
1               5                   10                  15

Glu Ala Asp Gly Tyr Pro Phe Gly Ile Val Lys Val Asp Glu Ser Gly
            20                  25                  30

Lys Ile Leu Leu Tyr Asn Lys Tyr Glu Ser Glu Leu Ala Asn Val Pro
        35                  40                  45

Ile Gln Thr Ala Val Gly Lys Asn Phe Phe Thr Glu Val Ala Ile Cys
    50                  55                  60

Thr Asn Asn Arg Ile Phe Tyr Gly Arg Phe Lys Glu Gly Met Ile Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Gly Thr Asn Ser
            100                 105                 110

Asn Trp Ile Phe Val Lys
            115

<210> SEQ ID NO 64
<211> LENGTH: 118
<212> TYPE: PRT
<213> ORGANISM: Leptospira meyeri

<400> SEQUENCE: 64

Phe Ile Asp Gln Asn Ile Ile Gly Lys Leu Gly Thr Leu Thr Gln Ser
1               5                   10                  15

```
Glu Ala Asp Ala Ala Ser Phe Gly Ile Val Lys Val Asp Gly Ser Gly
             20                  25                  30

Lys Ile Leu Leu Tyr Asn Lys Tyr Glu Ser Glu Leu Ala Asn Val Pro
         35                  40                  45

Ile Gln Thr Ala Val Gly Lys Asn Phe Phe Thr Glu Val Ala Ile Cys
    50                  55                  60

Thr Asn Asn Arg Ile Phe Tyr Gly Arg Phe Lys Glu Gly Met Val Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Asn Pro Ser Asn Thr
            100                 105                 110

Asn Trp Ile Phe Val Lys
        115
```

<210> SEQ ID NO 65
<211> LENGTH: 118
<212> TYPE: PRT
<213> ORGANISM: Leptospira yanagawae

<400> SEQUENCE: 65

```
Phe Ile Asp Pro Asn Ile Leu Gly Lys Leu Gly Thr Leu Gly Gln Ala
1               5                   10                  15

Asp Ala Asp Ser Tyr Pro Phe Gly Ile Val Lys Val Asp Glu Ser Gly
             20                  25                  30

Lys Ile Leu Leu Tyr Asn Lys Tyr Glu Ser Glu Leu Ala Asn Val Pro
         35                  40                  45

Ile Gln Thr Ala Val Gly Lys Asn Phe Phe Thr Glu Val Ala Ile Cys
    50                  55                  60

Thr Asn Asn Arg Ile Phe Tyr Gly Arg Phe Lys Glu Gly Met Ile Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Gly Thr Asn Thr
            100                 105                 110

Asn Trp Ile Phe Val Lys
        115
```

<210> SEQ ID NO 66
<211> LENGTH: 120
<212> TYPE: PRT
<213> ORGANISM: Salinibacter ruber DSM 13855

<400> SEQUENCE: 66

```
Leu Ala Phe Asp Asp Glu Gly Val Gly Glu Leu Arg His Val Asp
1               5                   10                  15

Glu Asp Glu Leu Asn Ala Ala Pro Phe Gly Ile Ile Gln Ile Asp Asp
             20                  25                  30

Ala Gly Val Val Gln Phe Tyr Asn Arg Tyr Glu Ser Asn Leu Ser Gly
         35                  40                  45

Ile Asp Pro Ala Asp Ala Val Gly Ala Asn Phe Thr Glu Leu Ala
    50                  55                  60

Pro Cys Ser Asn Asn Pro Leu Phe Gly Arg Phe Lys Asp Gly Val
65                  70                  75                  80

Arg Glu Gly Gly Leu Asp Glu Tyr Phe Thr Tyr Thr Phe Thr Tyr Gln
                85                  90                  95
```

Met Arg Pro Thr Leu Val Asp Val Arg Leu Tyr Arg Asp Glu Ala Glu
                100                 105                 110

Asn Asn Trp Ile Leu Ile Gln Lys
            115                 120

<210> SEQ ID NO 67
<211> LENGTH: 107
<212> TYPE: PRT
<213> ORGANISM: Burkholderia phytofirmans PsJN

<400> SEQUENCE: 67

Leu Ala Met Leu Asp Ala Asp Arg Leu Asp Gly Val Pro Phe Gly Val
1               5                   10                  15

Ile Gly Phe Thr Ser Asp Ala Leu Val Thr Val Tyr Asn Ala Thr Glu
                20                  25                  30

Ser Lys Asn Ala Gly Leu Arg Pro Lys Met Val Leu Gly Lys His Phe
            35                  40                  45

Phe Gly Glu Val Ala Pro Cys Met Asn Asn Phe Met Val Ala Gln Arg
        50                  55                  60

Phe Glu Asp Glu Asp Val Leu Asp Asp Ile Val Pro Tyr Val Leu Thr
65                  70                  75                  80

Leu Arg Met Arg Pro Thr Pro Val Arg Leu Arg Leu Leu Lys Ala Thr
                85                  90                  95

Asp Cys Ala Thr Arg Phe Val Leu Ile Glu Arg
                100                 105

<210> SEQ ID NO 68
<211> LENGTH: 123
<212> TYPE: PRT
<213> ORGANISM: Phaeospirillum fulvum

<400> SEQUENCE: 68

Met Thr Val Phe Ala Phe Asp Gln Ser Asp Pro Glu Asn Pro Leu Gly
1               5                   10                  15

Gln Leu Lys Asp Glu Asp Leu Arg Lys Ile Pro Tyr Gly Ala Ala Glu
                20                  25                  30

Leu Asn Ala Glu Gly Arg Val Val Ser Tyr Asn Asp Thr Glu Pro Glu
            35                  40                  45

Asp Asn Glu Ser Gly Arg Thr Ser Pro Val Gly Arg Asp Phe Phe Gly
        50                  55                  60

Asp Val Val Arg Trp Ala Gly Ser Ser Ile Ile Ala Ala Glu Phe Arg
65                  70                  75                  80

Lys Gly Val Thr Ser Gly Ala Leu Asn Val Val Phe Asp Cys Ala Ser
                85                  90                  95

Ala Arg Leu Pro Tyr Lys Val Arg Val His Phe Lys Val Ser Pro Ile
                100                 105                 110

Leu Gly Thr Tyr Trp Val Phe Ile Lys Arg Leu
            115                 120

<210> SEQ ID NO 69
<211> LENGTH: 121
<212> TYPE: PRT
<213> ORGANISM: Acidithiobacillus thiooxidans

<400> SEQUENCE: 69

Phe Val Ala Asp Ala Ile Leu Asn Asn Pro Asp Gln Ile Asn Ala Gln
1               5                   10                  15

Ile Ala Asp Arg Gln Ser Phe Gly Ile Ala Leu Asp Ser His Ala
                20                  25                  30

Gln Val Lys Ile Phe Asn Ala Ala Glu Ala Arg Leu Ser Gly Leu Ser
            35                  40                  45

Val Thr Glu Val Leu Gly Arg Asn Phe Phe Thr Glu Val Ala Pro Cys
50                  55                  60

Thr Ala Ser Arg Leu Phe Arg Gly Arg Phe Gln Gly Ile Gln Glu
65                  70                  75                  80

Gly Ser Leu Asp Ala His Phe Tyr Tyr Thr Phe Thr Tyr Arg Ile Arg
                85                  90                  95

Pro Ile Ser Ala His Val His Met Phe Tyr Asp Met Arg Lys Ser Pro
                100                 105                 110

Leu Phe Phe Ile Phe Ile Asp Arg Ile
                115                 120

<210> SEQ ID NO 70
<211> LENGTH: 126
<212> TYPE: PRT
<213> ORGANISM: Acidithiobacillus caldus SM-1

<400> SEQUENCE: 70

Met Pro Arg Lys Gly Phe Val Pro Gln Ala Ile Ser Glu His Leu Asp
1               5                   10                  15

Ser Leu Asn Gln Ala Leu Ala Asp Gln Gln Ser Phe Gly Ile Ile Gly
                20                  25                  30

Leu Asp Val Gln Ala Ile Val Arg Ile Phe Asn Lys Ala Glu Glu Arg
            35                  40                  45

Leu Ser Gly Leu Pro Ala Ser Glu Val Leu Asn His Ser Phe Phe Asp
50                  55                  60

Asp Val Ala Pro Cys Thr Ala Ser Arg Leu Phe Arg Gly Arg Phe Leu
65                  70                  75                  80

Ala Gly Leu Glu Arg Gly Ser Leu Asp Glu His Phe Phe Tyr Thr Phe
                85                  90                  95

Thr Tyr Arg Ile Arg Pro Val Ser Ala His Ile His Met Leu Tyr Arg
                100                 105                 110

Pro Ala Gln Ser Pro Leu Val Phe Leu Phe Val Asp Arg Val
            115                 120                 125

<210> SEQ ID NO 71
<211> LENGTH: 104
<212> TYPE: PRT
<213> ORGANISM: gamma proteobacterium NOR5-3

<400> SEQUENCE: 71

Thr Gln His Glu Leu Asp Asn Cys Asp Pro Asp Ala Leu Asp Phe Gly
1               5                   10                  15

Val Ile Arg Met Asp Arg Ser Gly Val Val Phe Tyr Asn Val Ala
                20                  25                  30

Glu Thr Arg Ile Ser Gly Leu Ser Lys Ser Gln Val Glu Gly Arg Ala
            35                  40                  45

Phe Phe Ser Glu Ile Gly Ile Cys Met His Asn Phe Met Val Gly His
50                  55                  60

Lys Phe Glu Gln Pro Gly Asp Leu Asp Glu Leu Val Asp Tyr Val Leu
65                  70                  75                  80

Thr Leu Arg Met Asp Pro Thr Pro Val Thr Leu Arg Leu Arg Gln
                85                  90                  95

```
Gly Asp Glu Lys Tyr Gln Tyr Leu
            100
```

<210> SEQ ID NO 72
<211> LENGTH: 125
<212> TYPE: PRT
<213> ORGANISM: Methylotenera versatilis 301

<400> SEQUENCE: 72

```
Met Asn Gln Ile Thr Phe Asp Met Leu Ser Leu Gly Gln Thr Leu Asp
1               5                   10                  15

Lys Leu Thr Asn Asp Gln Leu Asn Ser Leu Asp Phe Gly Val Ile Gly
            20                  25                  30

Phe Asp Asn Glu Gly Met Val Lys Val Tyr Asn Ala Tyr Glu Ser Lys
        35                  40                  45

Val Ala Gly Leu Ser Leu Glu Ser Val Ile Asp Ser Asp Leu Phe Asn
    50                  55                  60

Ser Val Ala Pro Cys Met Asn Asn Phe Met Val Ala Gln Lys Phe Glu
65                  70                  75                  80

Asp Ala Val Asp Thr Ser Ser Glu Leu Asp Glu Ile Met Asp Tyr Val
                85                  90                  95

Leu Thr Leu Lys Met Lys Pro Thr Arg Val Lys Leu Arg Leu Leu Ser
            100                 105                 110

Ser Pro Gln Phe Ser Tyr Ser Tyr Val Val Ile Leu Arg
        115                 120                 125
```

<210> SEQ ID NO 73
<211> LENGTH: 122
<212> TYPE: PRT
<213> ORGANISM: Leptothrix cholodnii SP-6

<400> SEQUENCE: 73

```
Leu Val Phe Asp Gln Pro Asp Leu Ala Ala Cys Ile Gly Thr Leu Ser
1               5                   10                  15

Glu Ala Gln Leu Asp Gly Leu Gly Phe Gly Val Ile Gly Phe Asp Ala
            20                  25                  30

Gln Gly Val Val Arg Val Tyr Asn Ala Phe Glu Ser Lys Tyr Ala Gly
        35                  40                  45

Leu Ser Pro Gln Arg Val Leu Gly His Pro Leu Phe Thr Val Val Ala
    50                  55                  60

Pro Cys Met Asn Asn Phe Met Val Ala Gln Arg Phe Glu Asp Ala Ala
65                  70                  75                  80

Ala Ser Ala Ala Ser Leu Asp Ala Thr Ile Asp Tyr Val Leu Thr Leu
                85                  90                  95

Arg Met Arg Pro Val Lys Val Lys Leu Arg Leu Leu Ala Ala Pro Ala
            100                 105                 110

Thr Ala Leu Arg Tyr Val Leu Val Gln Arg
        115                 120
```

<210> SEQ ID NO 74
<211> LENGTH: 119
<212> TYPE: PRT
<213> ORGANISM: Caenispirillum salinarum

<400> SEQUENCE: 74

```
Met Thr Phe Asp Asp Pro Asp Met Leu Arg Trp Leu Glu Ser Ala Arg
1               5                   10                  15

Ala Ala Asp Leu Asp Ala Leu Asp Phe Gly Val Ile Gly Ile Gly Pro
```

```
            20                  25                  30
Asp Gly Ala Val Ser His Tyr Asn Ala Trp Glu Val Glu Ala Ala Gly
             35                  40                  45

Ile Ser Arg Asp Trp Ala Met Gly Arg Asp Phe Phe Asn Glu Val Gly
 50                  55                  60

Leu Cys Met Asn Asn Phe Leu Val Ala Gln Arg Phe Glu Asp Glu Pro
 65                  70                  75                  80

Thr Leu Asp Ala Phe Val Asp Tyr Val Leu Thr Phe Arg Met Lys Pro
                 85                  90                  95

Thr Arg Val Thr Leu Arg Leu Leu Gln His Pro Asp Ser Pro Thr Arg
                100                 105                 110

Trp Ile Leu Ile Arg Arg Val
                115

<210> SEQ ID NO 75
<211> LENGTH: 125
<212> TYPE: PRT
<213> ORGANISM: Stigmatella aurantiaca DW4/3-1

<400> SEQUENCE: 75

Met Arg His Gly Ile Leu Glu Ala Glu Ser Leu Thr Glu Asp Arg Leu
 1               5                  10                  15

Gly Gln Leu Ser Pro Glu Glu Phe Asp Ala Leu Pro Phe Gly Ala Ile
             20                  25                  30

Lys Leu Asp Ala Glu Gly Arg Val Leu Ile Tyr Asn Ala Ala Glu Ser
             35                  40                  45

Ala Phe Ser Arg Arg Lys Pro Val Ser Val Leu Gly Arg Phe Phe
 50                  55                  60

Glu Glu Val Ala Pro Cys Thr Asn Val Ala Ser Phe Arg Gly Arg Phe
 65                  70                  75                  80

Asp Thr Leu Val Glu Arg Gly His Gly Thr Glu Ser Phe Asp Phe Gln
                 85                  90                  95

Phe Arg Phe Arg Trp Gly Thr Arg Asn Val Arg Ile Arg Leu Met Val
                100                 105                 110

Leu Gly Asp Gly Ser Arg Trp Val Phe Val Thr Ala Val
                115                 120                 125

<210> SEQ ID NO 76
<211> LENGTH: 122
<212> TYPE: PRT
<213> ORGANISM: Massilia timonae

<400> SEQUENCE: 76

Leu Ala Phe Asp Ala Pro Asp Leu Ala Ala Arg Leu Asp Gln Cys Thr
 1               5                  10                  15

Pro Glu Gln Leu Asp Ala Leu Asp Phe Gly Val Ile Gly Phe Gly Ala
             20                  25                  30

Asp Thr Asn Val Thr Leu Tyr Asn Ala Phe Glu Ser Gln Ala Ala Gly
             35                  40                  45

Leu Ser Pro Gln Arg Val Leu Gly Gln Pro Leu Phe Thr Asn Val Ala
 50                  55                  60

Pro Cys Met Asn Asn Phe Met Val Ala Gln Arg Phe Glu Asp Ala Gln
 65                  70                  75                  80

Glu Asp Asn Ser Val Leu Asp Ala Thr Ile Asp Tyr Val Leu Thr Leu
                 85                  90                  95

Arg Met Arg Pro Val Lys Val Ala Leu Arg Leu Leu Ser Asn Pro Gly
```

```
                    100                 105                 110
Gly Ser Arg Arg Tyr Val Leu Val Gln Arg
        115                 120

<210> SEQ ID NO 77
<211> LENGTH: 124
<212> TYPE: PRT
<213> ORGANISM: Methyloversatilis universalis FAM5

<400> SEQUENCE: 77

Gln Thr Val Ala Phe Ser Glu Ala Arg Met Leu Glu Phe Leu Glu Ser
1               5                   10                  15

Ala Ser Asp Glu Asp Leu Asp Arg Leu Asp Phe Gly Val Ile Gly Ile
            20                  25                  30

Asp Ala Gly Thr Asn Val Lys Arg Tyr Asn Arg Phe Glu Ser Ala Ala
        35                  40                  45

Ala Gly Leu Ser Lys Asp Arg Val Ile Gly Tyr Ala Leu Phe Thr Val
    50                  55                  60

Val Ala Pro Cys Met Asn Asn Phe Met Val Ala Gln Arg Phe Glu Asp
65                  70                  75                  80

Ala Gln Glu Gln Gly Ser Ala Leu Asp Asp Thr Ile Asp Tyr Val Leu
                85                  90                  95

Thr Leu Arg Met Arg Pro Val Lys Val Lys Leu Arg Leu Leu Ala Ala
            100                 105                 110

Pro Asp Arg Ala Leu Arg Tyr Val Leu Val Gln Arg
        115                 120

<210> SEQ ID NO 78
<211> LENGTH: 117
<212> TYPE: PRT
<213> ORGANISM: Spirosoma linguale DSM 74

<400> SEQUENCE: 78

Val His Phe Ser Asp Leu Asn Leu Leu Asp Trp Leu Glu Lys Gln Thr
1               5                   10                  15

Asn Glu Gln Leu Glu Asp Ala Pro Phe Gly Val Val Arg Met Ser Arg
            20                  25                  30

Asp Gly Ile Val Val Ala Tyr Cys Lys Ser Glu Ser His Ile Thr Gly
        35                  40                  45

Ile Ser Lys Glu Tyr Ala Val Gly Lys Tyr Tyr Phe Thr Gln Ile Ala
    50                  55                  60

Pro Cys Ala Asn Asn Gln Met Val Ala Ala Lys Tyr Ala Gln Pro Thr
65                  70                  75                  80

Leu Asp Glu Glu Leu Asp Tyr Ile Leu Thr Tyr Val Ser Glu Pro Thr
                85                  90                  95

Lys Val Arg Leu Arg Leu Leu Lys Ser Pro Glu Ser Arg Tyr Gln Tyr
            100                 105                 110

Phe Leu Val Asn Arg
        115

<210> SEQ ID NO 79
<211> LENGTH: 123
<212> TYPE: PRT
<213> ORGANISM: Rhodopseudomonas palustris BisB5

<400> SEQUENCE: 79

Met Asn Thr Val Asp Phe His Asp Ser Asp Leu Ala Arg Thr Ile Glu
1               5                   10                  15
```

```
Gln Leu Ala Pro Glu Gln Ile Asp Ala Leu Pro Phe Gly Val Ile Lys
             20                  25                  30

Leu Asp Gly Asn Gly Ile Val Thr Val Phe Asn Arg Thr Glu Ala Ile
         35                  40                  45

Glu Ser Gly Tyr Lys Ser Arg Pro Ala Leu Gly Leu Asp Phe Phe Leu
     50                  55                  60

Gln Val Ala Pro Cys Met Gly Gln Pro Glu Phe Arg Gly Arg Ile Glu
 65                  70                  75                  80

Gln Ala Arg Gln Leu Gly Arg Val Asp Ile Glu Leu Gly Trp Val Gly
                 85                  90                  95

Asp Phe Ser Asp Ile Asn Arg Ser Leu Gln Val Arg Ile Gln Ser Ala
             100                 105                 110

Ser Asp Gly Ser Leu Trp Ile Phe Asn Leu Arg
         115                 120

<210> SEQ ID NO 80
<211> LENGTH: 110
<212> TYPE: PRT
<213> ORGANISM: Sorangium cellulosum 'So ce 56'

<400> SEQUENCE: 80

Leu Asp Glu Arg Gly Leu Asp Ala Gln Pro Phe Gly Ile Ile Arg Leu
1               5                   10                  15

Asp Arg Glu Gly Thr Val Leu Ser Tyr Asn Leu Tyr Glu Leu Arg Gln
             20                  25                  30

Ala Arg Arg Asn Arg Gln Asp Val Ile Gly Lys Asn Phe Phe Thr Asp
         35                  40                  45

Ile Ala Pro Cys Ser Arg Val Lys Ala Phe His Gly Arg Phe Leu Ala
     50                  55                  60

Gly Val Glu Gln Arg Glu Leu Lys Ala Thr Phe Gly Phe Val Phe His
 65                  70                  75                  80

Phe Pro His Lys Thr Arg His Val Asp Val Ser Leu Phe Tyr Lys Ala
                 85                  90                  95

Ala Ala Arg Gln Gln Asp Asp Ala Val Trp Val Phe Ile Arg
             100                 105                 110

<210> SEQ ID NO 81
<211> LENGTH: 120
<212> TYPE: PRT
<213> ORGANISM: Rhodomicrobium vannielii ATCC 17100

<400> SEQUENCE: 81

Val Ser Phe Ala Asp Pro Lys Leu Ala Arg Lys Leu Glu Ala Leu Ser
1               5                   10                  15

Asp Glu Glu Arg His Asp Leu Pro Phe Gly Ile Ile Lys Leu Asp Ser
             20                  25                  30

Asn Gly Val Val Ser Phe Phe Ser Arg Thr Glu Ala Arg Glu Ser Gly
         35                  40                  45

Trp Lys Lys Arg Pro Ala Leu Gly Ile Asp Phe Phe Val Gly Ile Ala
     50                  55                  60

Pro Cys Met Ala Thr Pro Glu Phe Lys Gly Arg Ile Glu Glu Ala Ala
 65                  70                  75                  80

Arg His Gly Ala Val Asp Ile Glu Leu Gly Trp Val Gly Asp Phe Asp
                 85                  90                  95

Asp Pro Asn Gly Glu Met Thr Val Arg Ile Gln Ser Ala Ala Asp Gly
             100                 105                 110
```

Gly Ile Trp Ile Cys Leu Asp Arg
        115                 120

<210> SEQ ID NO 82
<211> LENGTH: 8
<212> TYPE: PRT
<213> ORGANISM: Artificial Sequence
<220> FEATURE:
<223> OTHER INFORMATION: Clone 2 - Region 94-101

<400> SEQUENCE: 82

Trp Leu Ile Pro Thr Leu Pro Gln
1               5

<210> SEQ ID NO 83
<211> LENGTH: 8
<212> TYPE: PRT
<213> ORGANISM: Artificial Sequence
<220> FEATURE:
<223> OTHER INFORMATION: Clone 3 - Region 94-101

<400> SEQUENCE: 83

Trp Met Ile Pro Thr Ser Arg Gly
1               5

<210> SEQ ID NO 84
<211> LENGTH: 8
<212> TYPE: PRT
<213> ORGANISM: Artificial Sequence
<220> FEATURE:
<223> OTHER INFORMATION: Clone 4 - Region 94-101

<400> SEQUENCE: 84

Trp Asp Ile Pro Thr Asn Pro Glu
1               5

<210> SEQ ID NO 85
<211> LENGTH: 8
<212> TYPE: PRT
<213> ORGANISM: Artificial Sequence
<220> FEATURE:
<223> OTHER INFORMATION: Clone 5 - Region 94-101

<400> SEQUENCE: 85

Trp Arg Ile Pro Thr Glu Cys Ala
1               5

<210> SEQ ID NO 86
<211> LENGTH: 8
<212> TYPE: PRT
<213> ORGANISM: Artificial Sequence
<220> FEATURE:
<223> OTHER INFORMATION: Clone 6 - Region 94-101

<400> SEQUENCE: 86

Trp Leu Ile Pro Thr Arg Asn Ala
1               5

<210> SEQ ID NO 87
<211> LENGTH: 8
<212> TYPE: PRT
<213> ORGANISM: Artificial Sequence
<220> FEATURE:
<223> OTHER INFORMATION: Clone 7 - Region 94-101

<400> SEQUENCE: 87

```
Trp Ser Ile Pro Ala Arg Ser Ala
1               5

<210> SEQ ID NO 88
<211> LENGTH: 8
<212> TYPE: PRT
<213> ORGANISM: Artificial Sequence
<220> FEATURE:
<223> OTHER INFORMATION: Clone 8 - Region 94-101

<400> SEQUENCE: 88

Trp Tyr Ile Pro Thr Gln Thr Ser
1               5

<210> SEQ ID NO 89
<211> LENGTH: 8
<212> TYPE: PRT
<213> ORGANISM: Artificial Sequence
<220> FEATURE:
<223> OTHER INFORMATION: Clone 9 - Region 94-101

<400> SEQUENCE: 89

Trp Met Ile Pro Thr Glu His Val
1               5

<210> SEQ ID NO 90
<211> LENGTH: 8
<212> TYPE: PRT
<213> ORGANISM: Artificial Sequence
<220> FEATURE:
<223> OTHER INFORMATION: Clone 10 - Region 94-101

<400> SEQUENCE: 90

Trp Ala Ile Pro Thr His Thr Gln
1               5

<210> SEQ ID NO 91
<211> LENGTH: 8
<212> TYPE: PRT
<213> ORGANISM: Artificial Sequence
<220> FEATURE:
<223> OTHER INFORMATION: Clone 11 - Region 94-101

<400> SEQUENCE: 91

Trp Ser Ile Pro Ala Gly Lys Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Clone 12 - Region 94-101

<400> SEQUENCE: 92

Trp Val Ile Pro Arg Glu Asp Asn
1               5

<210> SEQ ID NO 93
<211> LENGTH: 8
<212> TYPE: PRT
<213> ORGANISM: Artificial Sequence
<220> FEATURE:
<223> OTHER INFORMATION: Clone 13 - Region 94-101

<400> SEQUENCE: 93

Trp Ser Ile Pro Gln Ile Met Ala
```

```
<210> SEQ ID NO 94
<211> LENGTH: 8
<212> TYPE: PRT
<213> ORGANISM: Artificial Sequence
<220> FEATURE:
<223> OTHER INFORMATION: Clone 14 - Region 94-101

<400> SEQUENCE: 94

Trp Leu Val Pro Arg Ile Cys Gln
1               5

<210> SEQ ID NO 95
<211> LENGTH: 8
<212> TYPE: PRT
<213> ORGANISM: Artificial Sequence
<220> FEATURE:
<223> OTHER INFORMATION: Clone 15 - Region 94-101

<400> SEQUENCE: 95

Trp Thr Ile Pro Ala Leu Arg Lys
1               5

<210> SEQ ID NO 96
<211> LENGTH: 8
<212> TYPE: PRT
<213> ORGANISM: Artificial Sequence
<220> FEATURE:
<223> OTHER INFORMATION: Clone 16 - Region 94-101

<400> SEQUENCE: 96

Trp His Ile Pro Arg Asp Pro His
1               5

<210> SEQ ID NO 97
<211> LENGTH: 8
<212> TYPE: PRT
<213> ORGANISM: Artificial Sequence
<220> FEATURE:
<223> OTHER INFORMATION: Clone 17 - Region 94-101

<400> SEQUENCE: 97

Trp Ser Ile Pro Val Ser Gly Gln
1               5

<210> SEQ ID NO 98
<211> LENGTH: 8
<212> TYPE: PRT
<213> ORGANISM: Artificial Sequence
<220> FEATURE:
<223> OTHER INFORMATION: Clone 18 - Region 94-101

<400> SEQUENCE: 98

Trp Thr Val Pro Thr Phe Ile Val
1               5

<210> SEQ ID NO 99
<211> LENGTH: 8
<212> TYPE: PRT
<213> ORGANISM: Artificial Sequence
<220> FEATURE:
<223> OTHER INFORMATION: Clone 19 - Region 94-101

<400> SEQUENCE: 99

Trp Tyr Ile Pro Ala Asn His Lys
1               5
```

<210> SEQ ID NO 100
<211> LENGTH: 8
<212> TYPE: PRT
<213> ORGANISM: Artificial Sequence
<220> FEATURE:
<223> OTHER INFORMATION: Clone 20 - Region 94-101

<400> SEQUENCE: 100

Trp Val Ile Pro Pro Phe Glu Ser
1               5

<210> SEQ ID NO 101
<211> LENGTH: 8
<212> TYPE: PRT
<213> ORGANISM: Artificial Sequence
<220> FEATURE:
<223> OTHER INFORMATION: Clone 21 - Region 94-101

<400> SEQUENCE: 101

Trp Val Val Pro Asn Pro Ile Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Clone 22 - Region 94-101

<400> SEQUENCE: 102

Trp Gln Ile Pro Val Tyr Ala Val
1               5

<210> SEQ ID NO 103
<211> LENGTH: 8
<212> TYPE: PRT
<213> ORGANISM: Artificial Sequence
<220> FEATURE:
<223> OTHER INFORMATION: Clone 23 - Region 94-101

<400> SEQUENCE: 103

Trp Gln Ile Pro Thr Ser Ile Ile
1               5

<210> SEQ ID NO 104
<211> LENGTH: 8
<212> TYPE: PRT
<213> ORGANISM: Artificial Sequence
<220> FEATURE:
<223> OTHER INFORMATION: Clone 24 - Region 94-101

<400> SEQUENCE: 104

Trp Met Ile Pro Gly Asp Gly Asp
1               5

<210> SEQ ID NO 105
<211> LENGTH: 8
<212> TYPE: PRT
<213> ORGANISM: Artificial Sequence
<220> FEATURE:
<223> OTHER INFORMATION: Clone 25 - Region 94-101

<400> SEQUENCE: 105

Trp Asp Ile Pro His Asp Asp Ala
1               5

<210> SEQ ID NO 106
<211> LENGTH: 8
<212> TYPE: PRT
<213> ORGANISM: Artificial Sequence
<220> FEATURE:
<223> OTHER INFORMATION: Clone 26 - Region 94-101

<400> SEQUENCE: 106

Trp Ser Ile Pro Ser Val Arg His
1               5

<210> SEQ ID NO 107
<211> LENGTH: 8
<212> TYPE: PRT
<213> ORGANISM: Artificial Sequence
<220> FEATURE:
<223> OTHER INFORMATION: Clone 27 - Region 94-101

<400> SEQUENCE: 107

Trp Phe Ile Pro Lys Gly His Lys
1               5

<210> SEQ ID NO 108
<211> LENGTH: 8
<212> TYPE: PRT
<213> ORGANISM: Artificial Sequence
<220> FEATURE:
<223> OTHER INFORMATION: Clone 28 - Region 94-101

<400> SEQUENCE: 108

Trp Arg Ile Pro Lys Pro Thr Ala
1               5

<210> SEQ ID NO 109
<211> LENGTH: 8
<212> TYPE: PRT
<213> ORGANISM: Artificial Sequence
<220> FEATURE:
<223> OTHER INFORMATION: Clone 29 - Region 94-101

<400> SEQUENCE: 109

Trp Ala Val Pro Gly Val Cys Gly
1               5

<210> SEQ ID NO 110
<211> LENGTH: 8
<212> TYPE: PRT
<213> ORGANISM: Artificial Sequence
<220> FEATURE:
<223> OTHER INFORMATION: Clone 30 - Region 94-101

<400> SEQUENCE: 110

Trp Arg Ile Pro Gly Glu Met Phe
1               5

<210> SEQ ID NO 111
<211> LENGTH: 8
<212> TYPE: PRT
<213> ORGANISM: Artificial Sequence
<220> FEATURE:
<223> OTHER INFORMATION: Clone 31 - Region 94-101

<400> SEQUENCE: 111

Trp Ser Val Pro Thr Thr Arg Leu
1               5

-continued

```
<210> SEQ ID NO 112
<211> LENGTH: 8
<212> TYPE: PRT
<213> ORGANISM: Artificial Sequence
<220> FEATURE:
<223> OTHER INFORMATION: Clone 32 - Region 94-101

<400> SEQUENCE: 112

Trp Phe Val Pro Gly Pro Ser Val
1               5

<210> SEQ ID NO 113
<211> LENGTH: 8
<212> TYPE: PRT
<213> ORGANISM: Artificial Sequence
<220> FEATURE:
<223> OTHER INFORMATION: Clone 33 - Region 94-101

<400> SEQUENCE: 113

Trp Arg Ile Pro Arg Arg Val Val
1               5

<210> SEQ ID NO 114
<211> LENGTH: 8
<212> TYPE: PRT
<213> ORGANISM: Artificial Sequence
<220> FEATURE:
<223> OTHER INFORMATION: Clone 34 - Region 94-101

<400> SEQUENCE: 114

Trp Thr Leu Pro Ala Trp His His
1               5

<210> SEQ ID NO 115
<211> LENGTH: 8
<212> TYPE: PRT
<213> ORGANISM: Artificial Sequence
<220> FEATURE:
<223> OTHER INFORMATION: Clone 35 - Region 94-101

<400> SEQUENCE: 115

Trp Thr Ile Pro Val Leu Gly Thr
1               5

<210> SEQ ID NO 116
<211> LENGTH: 8
<212> TYPE: PRT
<213> ORGANISM: Artificial Sequence
<220> FEATURE:
<223> OTHER INFORMATION: Clone 36 - Region 94-101

<400> SEQUENCE: 116

Trp Glu Ile Pro Ile Pro Thr Asn
1               5

<210> SEQ ID NO 117
<211> LENGTH: 8
<212> TYPE: PRT
<213> ORGANISM: Artificial Sequence
<220> FEATURE:
<223> OTHER INFORMATION: Clone 37 - Region 94-101

<400> SEQUENCE: 117

Trp Val Ile Pro Asn Tyr Thr Met
1               5

<210> SEQ ID NO 118
```

```
<211> LENGTH: 8
<212> TYPE: PRT
<213> ORGANISM: Artificial Sequence
<220> FEATURE:
<223> OTHER INFORMATION: Clone 38 - Region 94-101

<400> SEQUENCE: 118

Trp Tyr Ile Pro Ala Leu His Trp
1               5

<210> SEQ ID NO 119
<211> LENGTH: 8
<212> TYPE: PRT
<213> ORGANISM: Artificial Sequence
<220> FEATURE:
<223> OTHER INFORMATION: Clone 39 - Region 94-101

<400> SEQUENCE: 119

Trp Gly Ile Pro Thr Pro Glu Glu
1               5

<210> SEQ ID NO 120
<211> LENGTH: 8
<212> TYPE: PRT
<213> ORGANISM: Artificial Sequence
<220> FEATURE:
<223> OTHER INFORMATION: Clone 40 - Region 94-101

<400> SEQUENCE: 120

Trp Glu Ile Pro Met Gly Ala His
1               5

<210> SEQ ID NO 121
<211> LENGTH: 8
<212> TYPE: PRT
<213> ORGANISM: Artificial Sequence
<220> FEATURE:
<223> OTHER INFORMATION: Clone 41 - Region 94-101

<400> SEQUENCE: 121

Trp Ser Ile Pro Pro Gly Arg Gln
1               5

<210> SEQ ID NO 122
<211> LENGTH: 8
<212> TYPE: PRT
<213> ORGANISM: Artificial Sequence
<220> FEATURE:
<223> OTHER INFORMATION: Clone 42 - Region 94-101

<400> SEQUENCE: 122

Trp Asn Leu Pro Val Lys Ala Pro
1               5

<210> SEQ ID NO 123
<211> LENGTH: 8
<212> TYPE: PRT
<213> ORGANISM: Artificial Sequence
<220> FEATURE:
<223> OTHER INFORMATION: Clone 43 - Region 94-101

<400> SEQUENCE: 123

Trp Glu Val Pro Ala Glu Thr Met
1               5

<210> SEQ ID NO 124
<211> LENGTH: 8
```

```
<212> TYPE: PRT
<213> ORGANISM: Artificial Sequence
<220> FEATURE:
<223> OTHER INFORMATION: Clone 44 - Region 94-101

<400> SEQUENCE: 124

Trp Arg Val Pro Asn Pro Thr Gly
1               5

<210> SEQ ID NO 125
<211> LENGTH: 8
<212> TYPE: PRT
<213> ORGANISM: Artificial Sequence
<220> FEATURE:
<223> OTHER INFORMATION: Clone 45 - Region 94-101

<400> SEQUENCE: 125

Trp Leu Ile Pro Lys Pro Phe Ile
1               5

<210> SEQ ID NO 126
<211> LENGTH: 8
<212> TYPE: PRT
<213> ORGANISM: Artificial Sequence
<220> FEATURE:
<223> OTHER INFORMATION: Clone 46 - Region 94-101

<400> SEQUENCE: 126

Trp Thr Val Pro Ser Thr Arg Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Clone 47 - Region 94-101

<400> SEQUENCE: 127

Arg Trp Ile Pro Gly Lys Met Val
1               5

<210> SEQ ID NO 128
<211> LENGTH: 8
<212> TYPE: PRT
<213> ORGANISM: Artificial Sequence
<220> FEATURE:
<223> OTHER INFORMATION: Clone 1 - Region 94-101

<400> SEQUENCE: 128

Trp Ile Ile Pro Thr Arg Asp Met
1               5

<210> SEQ ID NO 129
<211> LENGTH: 8
<212> TYPE: PRT
<213> ORGANISM: Artificial Sequence
<220> FEATURE:
<223> OTHER INFORMATION: Consensus sequence 94-101
<220> FEATURE:
<221> NAME/KEY: SITE
<222> LOCATION: 2
<223> OTHER INFORMATION: X is any amino acid
<220> FEATURE:
<221> NAME/KEY: SITE
<222> LOCATION: 6
<223> OTHER INFORMATION: X is any amino acid
<220> FEATURE:
<221> NAME/KEY: SITE
```

```
<222> LOCATION: 7
<223> OTHER INFORMATION: X is any amino acid
<220> FEATURE:
<221> NAME/KEY: SITE
<222> LOCATION: 8
<223> OTHER INFORMATION: X is any amino acid

<400> SEQUENCE: 129

Trp Xaa Ile Pro Thr Xaa Xaa Xaa
1               5
```